(12) United States Patent
Pachter et al.

(10) Patent No.: US 10,406,158 B2
(45) Date of Patent: *Sep. 10, 2019

(54) METHODS AND COMPOSITIONS FOR TREATING ABNORMAL CELL GROWTH

(71) Applicant: Verastem, Inc., Needham, MA (US)

(72) Inventors: Jonathan A. Pachter, Wayland, MA (US); Winnie Tam, Acton, MA (US); Qunli Xu, Wellesley, MA (US)

(73) Assignee: Verastem, Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/943,229

(22) Filed: Apr. 2, 2018

(65) Prior Publication Data

US 2019/0046531 A1 Feb. 14, 2019

Related U.S. Application Data

(63) Continuation of application No. 15/116,712, filed as application No. PCT/US2015/014843 on Feb. 6, 2015, now Pat. No. 9,962,385.

(60) Provisional application No. 61/937,253, filed on Feb. 7, 2014.

(51) Int. Cl.
| | |
|---|---|
| *A61K 31/506* | (2006.01) |
| *A61K 31/4184* | (2006.01) |
| *A61K 31/437* | (2006.01) |
| *A61K 31/44* | (2006.01) |
| *A61K 31/4523* | (2006.01) |
| *A61K 31/519* | (2006.01) |
| *A61K 31/06* | (2006.01) |
| *A61K 45/06* | (2006.01) |
| *A61K 9/00* | (2006.01) |

(52) U.S. Cl.
CPC .......... *A61K 31/506* (2013.01); *A61K 9/0053* (2013.01); *A61K 31/4184* (2013.01); *A61K 31/437* (2013.01); *A61K 31/44* (2013.01); *A61K 31/4523* (2013.01); *A61K 31/519* (2013.01); *A61K 45/06* (2013.01)

(58) Field of Classification Search
CPC .. A61K 31/506; A61K 31/184; A61K 31/437; A61K 31/44; A61K 31/4523; A61K 31/519; A61K 9/0053; A61K 45/06
See application file for complete search history.

(56) References Cited

U.S. PATENT DOCUMENTS

| | | |
|---|---|---|
| 2011/0086837 A1 | 4/2011 | Belvin et al. |
| 2013/0005964 A1 | 1/2013 | Luzzio et al. |
| 2014/0024653 A1 | 1/2014 | Debussche et al. |

FOREIGN PATENT DOCUMENTS

| | | |
|---|---|---|
| WO | WO-2012/045194 A1 | 4/2012 |
| WO | WO-2012095505 A1 | 7/2012 |
| WO | WO 2013170066 | * 11/2013 |
| WO | WO-2013170066 A1 | 11/2013 |
| WO | WO-2013182668 A1 | 12/2013 |
| WO | WO-2014059095 A1 | 4/2014 |

OTHER PUBLICATIONS

European Search Report for EP15746033 dated Aug. 18, 2017.
International Search Report for PCT/US2015/14843 dated Apr. 21, 2015.
Milella et al. "Beyond single pathway inhibition: MEK inhibitors as a a platform for the development of pharmacological combindations with synergistic anti-leukemic effects," Current Pharmaceutical Design, 2005, 11, 2779-2795.
Vu et al. "Green tea epigallocatechin gallate exhibits anticancer effect in human pancreatic carcinoma cells via the inhibition of both focal adhesion kinase and insulin-like growth factor-I receptor." Journal of Biomedicine and Biotechnology, 2010, 2010, 1-8.
El Touny, L. H. et al. "Combined SFK/MEK inhibition prevents metastatic outgrowth of dormant tumor cells" Journal of Clinical Investigation, Jan. 2014, vol. 124, No. 1, pp. 156-168.
Xu, Q. "Focal adhesion kinase (FAK) inhibitors VS-6063 and VS-4718 target cancer stem cells." Journal of Clinical Oncology, May 2013, vol. 31, No. 15 Suppl., Abstract No. e13523. doi:10.1200/jco.2013.31.15_suppl.e13523.
Ring, J. E. "Abstract B283: Defactinib (VS-6063) targets cancer stem cells directly and through inhibition of tumor-associated macrophages and cytokine production." Molecular Cancer Therapeutics, Nov. 2013, vol. 12, No. 11 Suppl., Abstract No. B283, doi:10.1158/1535-7163.TARG-13-B283.
Kolev, V. N. "Abstract A39: FAK inhibitors VS-6063 and VS-4718 preferentially target ovarian cancer stem cells." Clinical Cancer Research, Oct. 2013, vol. 19, No. 19 Suppl., Abstract No. A39.
Vidal, C. M. Abstract C271: FAK inhibitor defactinib (VS-6063) enhances the efficacy of paclitaxel and preferentially targets ovarian cancer stem cells. Molecular Cancer Therapeutics, Nov. 2013, vol. 12, No. 11 Suppl., Abstract No. C271, doi:10.1158/1535-7163.TARG-13-C271.
Patel, M. R. "Abstract A69: Phase 1/1b study of the FAK inhibitor defactinib (VS-6063) in combination with weekly paclitaxel for advanced ovarian cancer." Molecular Cancer Therapeutics, Nov. 2013, vol. 12, No. 11 Suppl., Abstract No. A69, doi:10.1158/1535-7163.TARG-13-A69.
Shapiro, I. M. "Abstract C262: Malignant mesothelioma lacking merlin shows enhanced sensitivity to the FAK inhibitor defactinib (VS-6063): Elucidation of the merlin-FAK relationship." Molecular Cancer Therapeutics, Nov. 2013, vol. 12, No. 11 Suppl., Abstract No. C262, doi:10.1158/1535-7163.TARG-13-C262.

(Continued)

*Primary Examiner* — Sahar Javanmard
(74) *Attorney, Agent, or Firm* — Goodwin Procter LLP

(57) ABSTRACT

The present invention relates to, inter alia, combinations, methods, compositions, and oral dosage forms of a FAK inhibitor and a MEK inhibitor, for treating abnormal cell growth (e.g., cancer).

11 Claims, 14 Drawing Sheets

(56) References Cited

OTHER PUBLICATIONS

Pachter, J. A. "Sensitivity of malignant mesothelioma lacking merlin to the FAK inhibitor VS-6063: Evaluation of merlin/NF2 status in clinical samples." Journal of Clinical Oncology, Nov. 2013, vol. 31, No. 15 Suppl., Abstract No. e18541, doi:10.1200/jco.2013.31.15_suppl.e18541.

Weaver, D. T. "Abstract A31: Merlin loss as a biomarker for defactinib (VS-6063) sensitivity: High frequency in malignant mesothelioma tumors." Molecular Cancer Therapeutics, Nov. 2013, vol. 12, No. 11 Suppl., Abstract No. A31, doi:10.1158/1535-7163.Targ-13-A31.

Matsumoto, S. "Combination efficacy of mTOR and MEK inhibitor in malignant pleural mesothelioma (MPM)." Journal of Clinical Oncology, 2013, vol. 31, No. 15 Suppl., Abstract No. e18557, doi:10.1200/jco.2013.31.15_suppl.e18557.

Miyoshi, S. et al. "Antitumor activity of MEK and PI3K inhibitors against malignant pleural mesothelioma cells in vitro and in vivo." International Journal of Oncology, 2012, vol. 41, No. 2, pp. 449-456.

Cole Jr. G. W. et al. "Suppression of Pro-metastasis phenotypes expression in malignant pleural mesothelioma by the PI3K inhibitor LY294002 or the MEK inhibitor UO126." Anticancer Research, 2006, vol. 26, No. 2A, pp. 809-821.

Akinleye A. et al. "MEK and the inhibitors: from bench to bedside." Journal of Hematology and Oncology, 2013, vol. 6, Article No. 27, pp. 1-11.

El-Khoueiry A. "Abstract B75: A first in-human phase I study to evaluate the MEK1/2 inhibitor GDC-0623 in patients with advanced solid tumors." Molecular Cancer Therapeutics, Nov. 2013, vol. 12, No. 11 Suppl., Abstract No. B75, doi:10.1158/1535-7163.TARG-13-B75.

Heist R. S. "Combination of a MEK inhibitor, pimasertib (MSC1936369B), and a PI3K/mTOR inhibitor, SAR 245409, in patients with advanced solid tumors: Results of a phase lb dose-escalation trial." Journal of Clinical Oncology, 2013, vol. 31, No. 15, Suppl., Abstract No. 2530.

Barkan D. et al. "Beta1-Integrin: A potential therapeutic target in the battle against cancer recurrence." Clinical Cancer Research, 2011, vol. 17, No. 23, pp. 7219-7223.

English translation of the Official Action dated Nov. 5, 2018 for Japanese patent application No. 2016-550218.

\* cited by examiner

US 10,406,158 B2

METHODS AND COMPOSITIONS FOR TREATING ABNORMAL CELL GROWTH

CLAIM OF PRIORITY

This application is a continuation application of U.S. patent application Ser. No. 15/116,712 filed on Aug. 4, 2016, which is a National Stage Application under 35 U.S.C. § 371 of international application number PCT/US2015/014843, filed on Feb. 6, 2015, which claims the benefit of and priority to U.S. Provisional Application No. 61/937,253 filed Feb. 7, 2014, each of which is herein incorporated by reference in their entirety.

BACKGROUND OF INVENTION

Convincing evidence suggests that focal adhesion kinase (FAK), a cytoplasmic, non-receptor tyrosine kinase, plays an essential role in cell-matrix signal transduction pathways (Clark and Brugge 1995, Science 268: 233-239) and its aberrant activation is associated with an increase in the metastatic potential of tumors (Owens et al. 1995, Cancer Research 55: 2752-2755). Selective inhibitors of certain non-receptor tyrosine kinases, such as FAK (focal adhesion kinase), lck, src, abl or serine/threonine kinases (e.g., cyclin dependent kinases), are useful in the treatment of abnormal cell growth, in particular cancer, in mammals. FAK is also known as the Protein-Tyrosine Kinase 2, PTK2. Compounds, compound combinations, compositions, and methods for inhibiting FAK in a subject are therefore desirable. FAK expression and/or activity has been reported to be upregulated in a range of malignancies, including cancers of the thyroid, prostate, cervix, colon, rectum, oral epithelium, ovary, and breast.

Components of the Ras/Raf/MEK/ERK signal transduction pathway also represent opportunities for the treatment of abnormal cell growth, e.g., cancer. MEK proteins are the primary downstream targets of Raf. The MEK family of genes consists of five genes: MEK1, MEK2, MEK3, MEK4, and MEK5. The MEK proteins belong to a family of dual-specificity kinases that have both serine/threonine and tyrosine kinase activity. MEK inhibitors have shown potential therapeutic benefit, for example, for inhibiting human tumor growth in nude mouse xenografts (Yeh, T. et al, Proceedings of the American Association of Cancer Research 2004, 45, Abs 3889). The MEK/ERK pathway has also been implicated in the self-renewal of cancer stem cells in breast and prostate cancer (Balko et al, Cancer Research 2013; Rybak et al, PLoS One 2013).

SUMMARY OF INVENTION

Applicants have discovered certain combinations (e.g., a combination as described herein, e.g., a FAK inhibitor in combination with a MEK inhibitor), which can be used, for example to treat abnormal cell growth, such as cancer, in humans.

In one aspect, the present invention comprises a method of treating a subject having cancer, the method comprising administering to the subject a therapeutically effective amount of a FAK inhibitor (e.g., VS-6063, or a pharmaceutically acceptable salt thereof), in combination with a MEK inhibitor (e.g., GDC-0623, cobimetinib, trametinib, pimasertib, AZD6244), thereby treating the subject. In some embodiments, the FAK inhibitor or the MEK inhibitor is administered orally (e.g., the FAK inhibitor and the MEK inhibitor are administered orally).

In some embodiments, the subject is a human.

In some embodiments, the FAK inhibitor is VS-6063, or a pharmaceutically acceptable salt thereof. In some embodiments, VS-6063, or a pharmaceutically acceptable salt thereof is administered at from 10 to 2000 mg, 50 to 1500 mg, 100 to 1000 mg, 500 to 1000 mg, or 700 to 900 mg, per day. In some embodiments, VS-6063, or a pharmaceutically acceptable salt thereof is administered at from 10 to 1000 mg, 50 to 750 mg, 100 to 750 mg, 250 to 500 mg, or 300 to 500 mg, twice daily. In some embodiments, VS-6063, or a pharmaceutically acceptable salt thereof is administered in an amount of at least 10, 25, 50, 100, 150, 200, 250, 500, 750, or 800 mg/day. In some embodiments, VS-6063, or a pharmaceutically acceptable salt thereof is administered in an amount of at least 10, 25, 50, 100, 150, 200, 250, 400 mg/twice daily. In some embodiments, VS-6063, or a pharmaceutically acceptable salt thereof is administered in an amount of 1500, 1000, 800 or less mg/day. In some embodiments, VS-6063, or a pharmaceutically acceptable salt thereof is administered in an amount of 750, 500, 400 or less mg/twice daily. In some embodiments, VS-6063, or a pharmaceutically acceptable salt thereof is administered as a composition (e.g., a pharmaceutical composition such as in an oral dosage form). In some embodiments, VS-6063, or a pharmaceutically acceptable salt thereof is present in the composition (e.g., a pharmaceutical composition such as in an oral dosage form) comprising 5 to 30%, 10 to 30%, 10 to 20%, 12 to 15%, 13% weight of VS-6063, or a pharmaceutically acceptable salt thereof, per weight of the composition.

In some embodiments, the MEK inhibitor is trametinib, or a pharmaceutically acceptable salt thereof. In some embodiments, the MEK inhibitor is GDC-0623, or a pharmaceutically acceptable salt thereof. In some embodiments, the MEK inhibitor is cobimetinib, or a pharmaceutically acceptable salt thereof. In some embodiments, the MEK inhibitor is AZD6244, or a pharmaceutically acceptable salt thereof. In some embodiments, the MEK inhibitor is pimasertib, or a pharmaceutically acceptable salt thereof. In some embodiments, pimasertib, or a pharmaceutically acceptable salt thereof is administered at between 1 to 500 mg, 1 to 250 mg, 1 to 100 mg, 1 to 75 mg, 5 to 500 mg, 5 to 250 mg, 5 to 100 mg, 5 to 75 mg, 10 to 500 mg, 10 to 250 mg, 10 to 100 mg, 10 to 75 mg, per day. In some embodiments, pimasertib, or a pharmaceutically acceptable salt. thereof is administered at least 1, 5, 10, 25, or 50 mg/day. In some embodiments, pimasertib, or a pharmaceutically acceptable salt thereof is administered 150, 100, 60 or less mg/day. In some embodiments, pimasertib, or a pharmaceutically acceptable salt thereof is administered as a composition (e.g., an oral dosage form).

In some embodiments, the cancer is a solid tumor, soft tissue tumor, metastasis, or non-solid cancer. In some embodiments, the cancer is solid tumor. In some embodiments, the solid tumor is a malignancy (e.g., sarcomas, adenocarcinomas, and carcinomas) of an organ (e.g., of lung, breast, lymphoid, gastrointestinal (e.g., colon), and genitourinary (e.g., renal, urothelial, or testicular tumors) tracts, pharynx, prostate, and ovary). In some embodiments, the cancer is a mesothelioma; neurofibromatosis; e.g., neurofibromatosis type 2, neurofibromatosis type 1; renal cancer; lung cancer, non small cell lung cancer; liver cancer; thyroid cancer; ovarian; breast cancer; a nervous system tumor; schwannoma: meningioma; schwannomatosis; neuroma acoustic; adenoid cystic carcinoma; ependymoma; ependymal tumors, or any other tumor which exhibits decreased merlin expression and/or mutation, and/or deletion and/or promotor hypermethylation of the NF-2 gene. In some embodiments, the cancer is selected from the group comprising mesothelioma (e.g., malignant pleural mesothelioma, e.g., surgical resectable malignant pleural mesothelioma), breast cancer (e.g., triple negative breast cancer), ovarian cancer (e.g., advanced ovarian cancer), lung cancer (e.g., non-small cell lung cancer (NSCLC), e.g., KRAS mutant NSCLC)), and non-hematolotic malignancies. In some embodiments, the cancer is selected from the group comprising melanoma (e.g., N-Ras mutated locally advanced or metastasis malignant cutaneous melanoma), colorectal cancer (e.g., metastatic colorectal cancer), leukemia (e.g., acute myeloid leukemia), adenocarcinoma (e.g., pancreatic adenocarcinoma), solid tumor (e.g., locally advanced solid tumor, metastatic solid tumor, hepatocellular carcinoma).

In some embodiments, the FAK inhibitor and the MEK inhibitor are administered at amounts (e.g., doses) that result in a synergistic (e.g., therapeutic) effect.

In some embodiments, the administration is performed in combination with administration of an additional agent (e.g., cancer therapeutic, e.g., a standard of care cancer therapeutic, e.g., taxane, e.g., paclitaxel). In some embodiments, the additional agent is a cancer therapy (e.g., a first-line therapy, standard of care treatment). In some embodiments, the cancer therapy is chemotherapy, targeted therapies (e.g., antibody therapies), immunotherapy, or hormonal therapy. In some embodiments, the cancer therapy comprises administration of an anti-inflammatory agent, analgesic agent, or antiemetic agent.

In one aspect, the present invention comprises a composition or dosage form comprising a FAK inhibitor and a MEK inhibitor, wherein the inhibitors are present in each case in free form or in the form of a pharmaceutically acceptable salt or hydrate thereof, and optionally at least one pharmaceutically acceptable carrier, for simultaneous, separate, or sequential use.

In one aspect, the present invention comprises a composition or dosage form comprising a FAK inhibitor and a MEK inhibitor, wherein the inhibitors are present in each case in free form or in the form of a pharmaceutically acceptable salt or hydrate thereof, and wherein the inhibitors are present in a synergistic ratio.

In one aspect, the present invention comprises a composition or dosage form comprising a therapeutically effective amount of a FAK inhibitor (e.g., VS-6063, or a pharmaceutically acceptable salt thereof) and a MEK inhibitor (e.g., GDC-0623, cobimetinib, trametinib, pimasertib, AZD6244).

In some embodiments, the FAK inhibitor is VS-6063, or a pharmaceutically acceptable salt thereof. In some embodiments, VS-6063, or a pharmaceutically acceptable salt thereof is administered at 400 or less mg/twice daily.

In some embodiments, the MEK inhibitor is trametinib, or a pharmaceutically acceptable salt. thereof. In some embodiments, the MEK inhibitor is GDC-0623, or a pharmaceutically acceptable salt thereof. In some embodiments, the MEK inhibitor is cobimetinib, or a pharmaceutically acceptable salt thereof. In some embodiments, the MEK inhibitor is AZD6244, or a pharmaceutically acceptable salt thereof. In some embodiments, the MEK inhibitor is pimasertib, or a pharmaceutically acceptable salt thereof. In some embodiments, pimasertib, or a pharmaceutically acceptable salt thereof is administered at 60 or less mg/daily.

DETAILED DESCRIPTION OF THE INVENTION

Figure 1A:
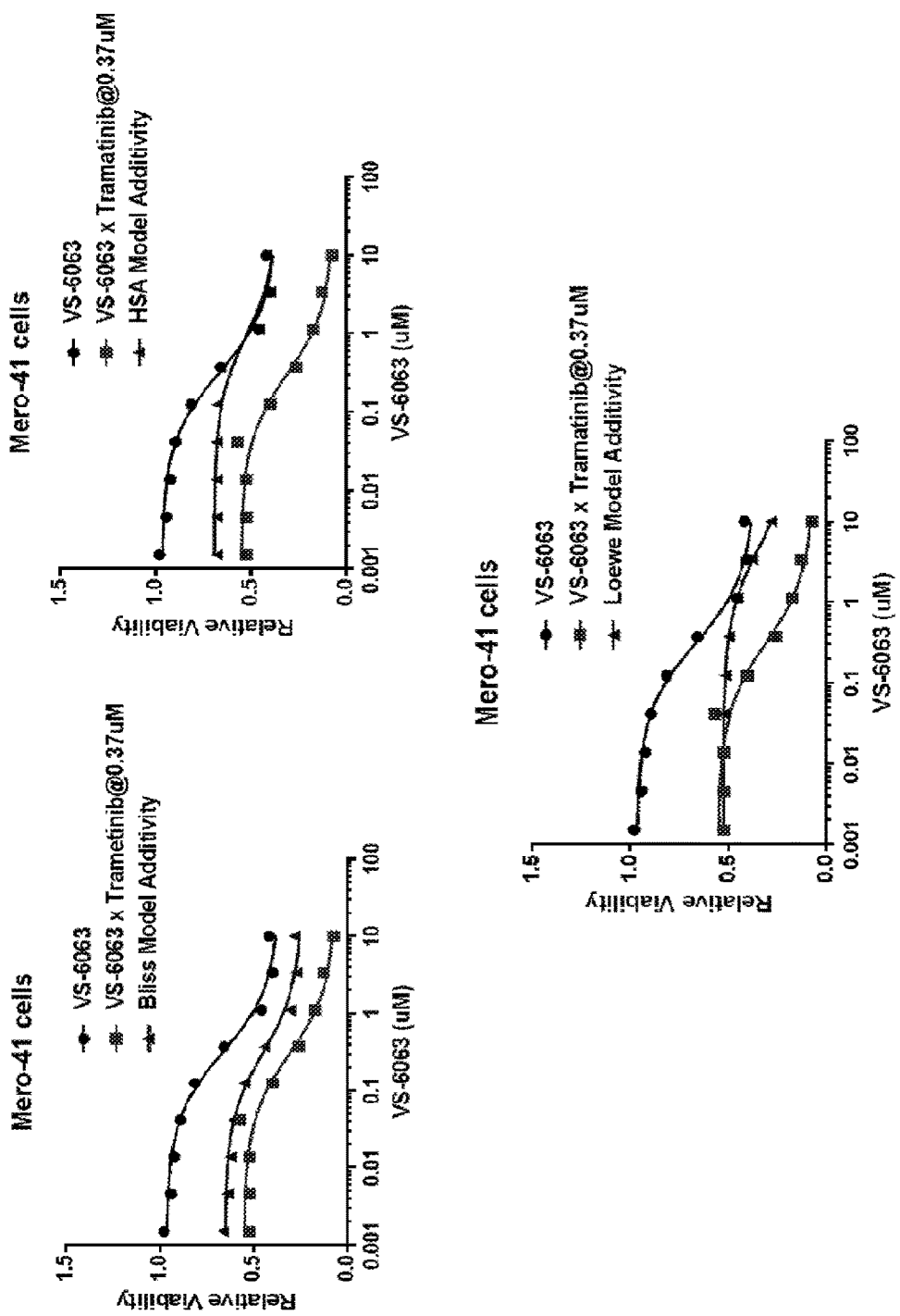
FIGS. 1A and 1B show exemplary plots of mesothelioma cell viability with increasing concentrations of VS-6063, an exemplary FAK inhibitor, with and without tramatinib, an exemplary MEK inhibitor.

This disclosure is not limited in its application to the details of the methods and compositions described herein. Also, the phraseology and terminology used herein is for the purpose of description and should not be regarded as limiting.

Definitions

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, an amount of a compound or combination effective to treat a disorder (e.g., a disorder as described herein), "therapeutically effective amount", "effective amount" or " effective course" refers to an amount of the compound or combination which is effective, upon single or multiple dose administration(s) to a subject, in treating a subject, or in curing, alleviating, relieving or improving a subject with a disorder (e.g., a disorder as described herein) beyond that expected in the absence of such treatment (e.g., placebo treatment).

The term "pharmaceutically acceptable," as used herein, refers to a compound or carrier (e.g., excipient) that may be administered to a subject, together with a compound described herein (e.g., a FAK inhibitor, a MEK inhibitor), and which does not destroy the pharmacological activity thereof and is nontoxic when administered in doses sufficient to deliver a therapeutic amount of the compound.

The term, "pharmaceutically acceptable salts," as used herein, refers to derivatives of a compound described herein (e.g., a FAK inhibitor, a MEK inhibitor), wherein the compound is modified by converting an existing acid or base moiety to its salt form. Examples of pharmaceutically acceptable salts include, but are not limited to, mineral or organic acid salts of basic residues such as amines: alkali or organic salts of acidic residues such as carboxylic acids; and the like. The pharmaceutically acceptable salts of the disclosure include the conventional non-toxic salts of a compound described herein (e.g., a FAK inhibitor, a MEK inhibitor), formed, for example, from non-toxic inorganic or organic acids. The pharmaceutically acceptable salts of the disclosure can be synthesized from a compound described herein (e.g., a FAK inhibitor, a MEK inhibitor), which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The phrase, "pharmaceutically acceptable derivative or prodrug," as used herein refers to any pharmaceutically acceptable salt, ester, salt of an ester, or other derivative of a compound, e.g., a FAK inhibitor, a MEK inhibitor, which, upon administration to a recipient, is capable of providing (directly or indirectly) a therapeutic agent. Particularly favored derivatives and prodrugs are those that increase the bioavailability of a compound described herein (e.g., a FAK inhibitor, a MEK inhibitor) when such compounds are administered to a mammal (e.g., by allowing an orally administered compound to be more readily absorbed into the blood) or which enhance delivery of a compound described herein (e.g., a FAK inhibitor, a MEK inhibitor) to a biological compartment, e.g., relative to general distribution of a compound described herein (e.g., a FAK inhibitor, a MEK inhibitor). Preferred prodrugs include derivatives where a group which enhances aqueous solubility or active transport through the gut membrane is appended to the structure of the formulae of the compounds described herein (e.g., a FAK inhibitor, a MEK inhibitor).

The term, "oral dosage form," as used herein, refers to a composition or medium used to administer an agent, e.g., VS-6063, to a subject. Typically, an oral dosage form is administered via the mouth, however, "oral dosage form" is intended to cover any substance which is administered to a subject and is absorbed across a membrane, e.g., a mucosal membrane, of the gastrointestinal tract, including, e.g., the mouth, esophagus, stomach, small intestine, large intestine, and colon. For example, "oral dosage form" covers a solution which is administered through a feeding tube into the stomach.

The term, "treat" or "treatment," as used herein, refers to the application or administration of a compound, alone or in combination with, an additional agent to a subject, e.g., a subject who has a disorder (e.g., a disorder as described herein), a symptom of a disorder, or a predisposition toward a disorder, with the purpose to cure, heal, alleviate, relieve, alter, remedy, ameliorate, improve or affect the disorder.

As used herein, the phrase "synergistic effect" refers to a greater than additive effect (e.g., therapeutic effect) of two or more compounds or compositions. An exemplary synergistic effect includes administration of an amount of a FAK inhibitor (e.g., VS-6063, or a pharmaceutically acceptable salt thereof) used (e.g., administered) in combination with an amount of a MEK inhibitor (e.g., pimasertib, or a pharmaceutically acceptable salt thereof) that results in a therapeutic effect that is greater than the additive therapeutic effect of each inhibitor used alone.

As used herein, the term "subject" is intended to include human and non-human animals. Exemplary human subjects include a human subject having a disorder, e.g., a disorder described herein. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Combinations

The present invention relates to, inter alia, combinations of a FAK inhibitor and a MEK inhibitor (i.e., a FAK inhibitor in combination with a MEK inhibitor), and methods for treating abnormal cell growth, e.g., cancer, comprising administering to a subject in need thereof, a FAK inhibitor in combination with a MEK inhibitor.

The phrase, "in combination with," and the terms "co-administration," "co-administering," or "co-providing", as used herein in the context of the administration of a compound described herein or a therapy described herein, means that two (or more) different compounds or therapies are delivered to the subject during the course of the subject's affliction with the disease or disorder (e.g., a disease or disorder as described herein, e.g., cancer), e.g., two (or more) different compounds or therapies are delivered to the subject after the subject has been diagnosed with the disease or disorder (e.g., a disease or disorder as described herein, e.g., cancer) and before the disease or disorder has been cured or eliminated or treatment. has ceased for other reasons. In some embodiments, the delivery of one compound or therapy is still occurring when the delivery of the second begins, so that there is overlap in terms of administration. This is sometimes referred to herein as "simultaneous" or "concurrent delivery." In other embodiments, the delivery of one compound or therapy ends before the delivery of the other compound or therapy begins. In some embodiments of either case, the treatment (e.g., administration of compound, composition, or therapy) is more effective because of combined administration. For example, the second compound or therapy is more effective, e.g., an equivalent effect is seen with less of the second compound or therapy, or the second compound or therapy reduces symptoms to a greater extent, than would be seen if the second compound or therapy were administered in the absence of the first compound or therapy, or the analogous situation is seen with the first compound or therapy. In some embodiments, delivery is such that the reduction in a symptom, or other parameter related to the disorder is greater than what would be observed with one compound or therapy delivered in the absence of the other. The effect of the two compounds or therapies can be partially additive, wholly additive, or great than additive (e.g., synergistic). The delivery can be such that the first compound or therapy delivered is still detectable when the second is delivered.

In some embodiments, the first compound or therapy and second compound or therapy can be administered simultaneously (e.g., at the same time), in the same or in separate compositions, or sequentially. Sequential administration refers to administration of one compound or therapy before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional, e.g., secondary, compound or therapy. The order of administration of the first and secondary compound or therapy can also be reversed.

The combinations described herein, e.g., a FAK inhibitor in combination with a MEK inhibitor, can be a first line treatment for abnormal cell growth, e.g., cancer, i.e., it is used in a patient who has not been previously administered another drug intended to treat the cancer; a second line treatment for the cancer, i.e., it is used in a subject in need thereof who has been previously administered another drug intended to treat the cancer; a third or fourth treatment for the cancer, i.e., it is used in a subject who has been previously administered two or three other drugs intended to treat the cancer.

In some embodiments, the combinations described herein, e.g., a FAK inhibitor in combination with a MEK inhibitor, is a first line treatment for the cancer. In some embodiments, the combinations described herein, e.g., a FAK inhibitor in combination with a MEK inhibitor, is a second line treatment for the cancer.

FAK Inhibitors
Compound VS-6063
An example of a FAK inhibitor is the compound VS-6063 (e.g., VS-6063 free base):

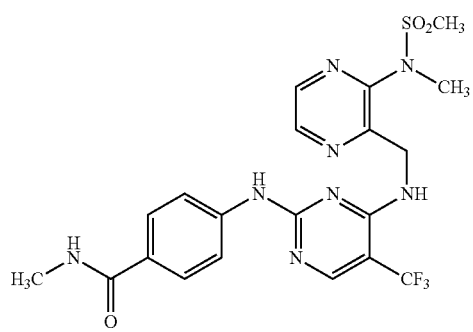

or a pharmaceutically acceptable salt thereof (e.g., VS-6063 hydrochloride), as disclosed in U.S. Pat. No. 7,928,109. VS-6063 is also known as defactinib or PF-04554878.

VS-6063 is a potent inhibitor of the FAK protein tyrosine kinases, and may be adapted to therapeutic use as antiproliferative agents (e.g., anticancer), antitumor (e.g., effective against solid tumors), antiangiogenesis (e.g., stop or prevent proliferation of blood vessels) in mammals, particularly in humans. VS-6063 may be useful in the prevention and treatment of non-hematolotic malignancies. Moreover, VS-6063 may be useful in the prevention and treatment of a variety of human hyperproliferative disorders, including malignant and benign tumors of the liver, kidney, bladder, breast, gastric, ovarian, colorectal, prostate, pancreatic, lung, vulval, thyroid., hepatic carcinomas, sarcomas, glioblastomas, head and neck, and other hyperplastic conditions such as benign hyperplasia of the skin (e.g., psoriasis) and benign hyperplasia of the prostate (e.g., BPH). VS-6063 may also be useful in the prevention and treatment of disorders such as mesothelioma.

MEK Inhibitors

A MEK inhibitor can be a small molecule or biologic inhibitor of the mitogen-activated protein kinase (MAPK) enzymes MEK1 and/or MEK2 (e.g., MAPK/ERK pathway).

Examples of MEK inhibitors include:
Trametinib (also known as Mekinst. GSK1120212)

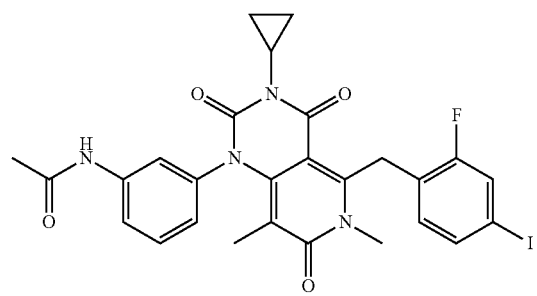 [SMILES: CC(=O)Nc1cccc(-n2c(=O)n(C3CC3)c(=O)c3c(Cc4ccc(I)cc4F)n(C)c(=O)c(C)c32)c1]

Pimasertib (also known as AS703026, MSC1936369B):

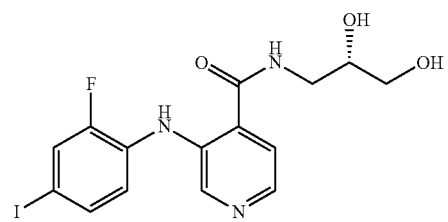 [SMILES: O=C(NC[C@H](O)CO)c1ccncc1Nc1ccc(I)cc1F]

GDC-0623 is a selective MEK inhibitor with potential antineoplastic activity. MEK inhibitor GDC-0623 specifically inhibits mitogen-activated protein kinase kinase (MEK or MAP/ERK kinase), resulting in inhibition of growth factor-mediated cell signaling and tumor cell proliferation. MEK is a key component of the RAS/RAF/MEK/ERK signaling pathway that regulates cell growth; constitutive activation of this pathway has been implicated in many cancers. Hatzivassiliou et al. Nature 2013, 501 (7466), 232-6.

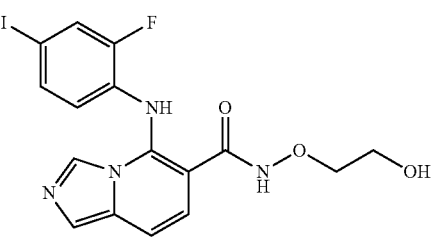 [SMILES: O=C(NOCCO)c1ccc2cncn2c1Nc1ccc(I)cc1F]

Cobimetinib (also known as GDC-0973, XL-518)

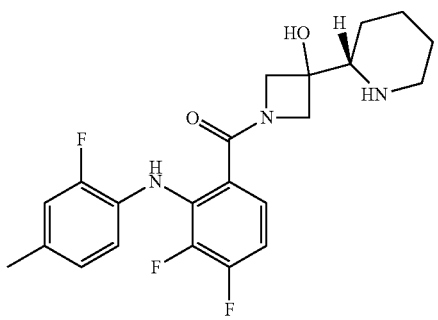 [SMILES: Cc1ccc(Nc2c(C(=O)N3CC(O)([C@@H]4CCCCN4)C3)ccc(F)c2F)c(F)c1]

Selumetinib (also known as AZD6244, ARRY-142886)

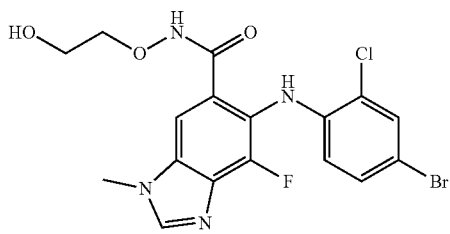 [SMILES: Cn1cnc2c(F)c(Nc3ccc(Br)cc3Cl)c(C(=O)NOCCO)cc21]

MEK162 (also known as ARRY-162, ARRY-438162)

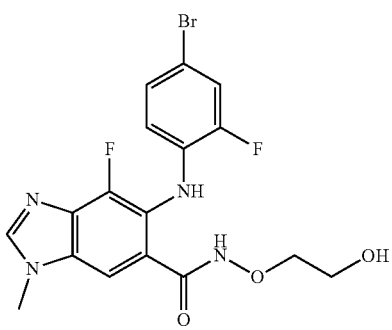 [SMILES: Cn1cnc2c(F)c(Nc3ccc(Br)cc3F)c(C(=O)NOCCO)cc21]

PD-325901

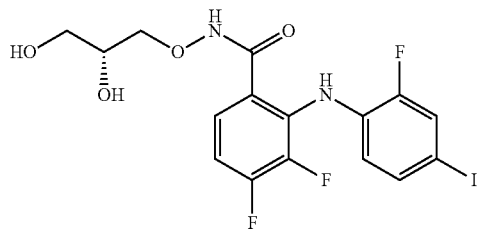 [SMILES: O=C(NOC[C@H](O)CO)c1ccc(F)c(F)c1Nc1ccc(I)cc1F]

CI-1040

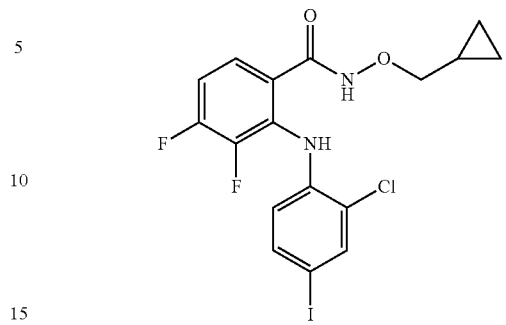

In some embodiments, the MEK inhibitor is Pimasertib (also known as AS703026, MSC1936369B). In some embodiments, the MEK inhibitor is Trametinib (also known as Mekinst, GSK1120212). In some embodiments, the MEK inhibitor is GDC-0623. In some embodiments, the MEK inhibitor is AZD6244. In some embodiments, the MEK inhibitor is Cobimetinib (also known as GDC-0973, XL-518). In some embodiments, the MEK inhibitor is Selumetinib (also known as AZD6244, ARRY-142886). In some embodiments, the MEK inhibitor is MEK162 (also known as ARRY-162, ARRY-438162).

Disease and Disorders

Abnormal Cell Growth

Abnormal cell growth, as used herein and unless otherwise indicated, refers to cell growth that is independent of normal regulatory mechanisms (e.g., loss of contact inhibition). This includes the abnormal growth of: (1) tumor cells (tumors) that proliferate, for example, by expressing a mutated tyrosine kinase or overexpression of a receptor tyrosine kinase; (2) benign and malignant cells of other proliferative diseases, for example, in which aberrant tyrosine kinase activation occurs; (3) any tumors that proliferate, for example, by receptor tyrosine kinases; (4) any tumors that proliferate, for example, by aberrant serine/threonine kinase activation; and (5) benign and malignant cells of other proliferative diseases, for example, in which aberrant serine/threonine kinase activation occurs. Abnormal cell growth can refer to cell growth in epithelial (e.g., carcinomas, adenocarcinomas); mesenchymal (e.g., sarcomas (e.g. leiomyosarcoma, Ewing's sarcoma)); hematopoetic (e.g., lymphomas, leukemias, myelodysplasias (e.g., pre-malignant)); or other (e.g., melanoma, mesothelioma, and other tumors of unknown origin) cells.

Neoplastic Disorders

Abnormal cell growth can refer to a neoplastic disorder. A "neoplastic disorder" is a disease or disorder characterized by cells that have the capacity for autonomous growth or replication, e.g., an abnormal state or condition characterized by proliferative cell growth. An abnormal mass of tissue as a result of abnormal cell growth or division, or a "neoplasm," can be benign, pre-malignant (carcinoma in situ) or malignant (cancer).

Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Treatment with the compound may be in an amount effective to ameliorate at least one symptom of the neoplastic disorder, e.g., reduced cell proliferation, reduced tumor mass, etc.

Cancer

The inventive methods of the present invention may be useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer (e.g., Hepatocellular carcinoma), non-small cell carcinoma of the lung, pancreatic (e.g., metastatic pancreatic adenocarcinoma) and cancer of the small intestine.

The cancer can include mesothelioma; neurofibromatosis; e.g., neurofibromatosis type 2, neurofibromatosis type 1; renal cancer; lung cancer, non small cell lung cancer; liver cancer; thyroid cancer; ovarian; breast cancer; a nervous system tumor; schwannoma; meningioma; schwannomatosis; neuroma acoustic; adenoid cystic carcinoma; ependymoma; ependymal tumors, or any other tumor which exhibits decreased merlin expression and/or mutation, and/ or deletion and/or promotor hypermethylation of the NF-2 gene. In some embodiments, the cancer is renal cancer.

The cancer can include cancers characterized as comprising cancer stem cells, cancer associated mesenchymal cells, or tumor initiating cancer cells. The cancer can include cancers that have been characterized as being enriched with cancer stem cells, cancer associated mesenchymal cells, or tumor initiating cancer cells (e.g., a tumor enriched with cells that have undergone an epithelial-to-mesenchymal transition or a metastatic tumor).

The cancer can be a primary tumor, i.e., located at the anatomical site of tumor growth initiation. The cancer can also be metastatic, i.e., appearing at least a second anatomical site other than the anatomical site of tumor growth initiation. The cancer can be a recurrent cancer, i.e., cancer that returns following treatment, and after a period of time in which the cancer was undetectable. The recurrent cancer can be anatomically located locally to the original tumor, e.g., anatomically near the original tumor; regionally to the original tumor, e.g., in a lymph node located near the original tumor; or distantly to the original tumor, e.g., anatomically in a region remote from the original tumor.

The cancer can also include for example, but is not limited to, epithelial cancers, breast, lung, pancreatic, colorectal (e.g., metastatic colorectal, e.g., metastatic K Ras mutated), prostate, head and neck, melanoma (e.g., N Ras mutated locally advanced or metastatic malignant cutaneous melanoma), acute myelogenous leukemia, and glioblastoma. Exemplary breast cancers include triple negative breast cancer, basal-like breast cancer, claudin-low breast cancer, invasive, inflammatory, metaplastic, and advanced Her-2 positive or ER-positive cancers resistant to therapy.

Other cancers include but are not limited to, brain, abdominal, esophagus, gastrointestinal, glioma, liver, tongue, neuroblastoma, osteosarcoma, ovarian, retinoblastoma, Wilm's tumor, multiple myeloma, skin, lymphoma, blood and bone marrow cancers (e.g., advanced hematological malignancies, leukemia, e.g., acute myeloid leukemia (e.g., primary or secondary), acute lymphoblastic leukemia, acute lymphocytic leukemia, T cell leukemia, hematological malignancies, advanced myeloproliferative disorders, myelodysplastic syndrome, relapsed or refractory multiple myeloma, advanced myeloproliferative disorders), retinal, bladder, cervical, kidney, endometrial, meningioma, lymphoma, skin, uterine, lung, non small cell lung, nasopharyngeal carcinoma, neuroblastoma, solid tumor, hematologic malignancy, squamous cell carcinoma, testicular, thyroid, mesothelioma, brain vulval, sarcoma, intestine, oral, endocrine, salivary, spermatocytic seminoma, sporadic medulalry thyroid carcinoma, non-proliferating testes cells, cancers related to malignant mast cells, non-Hodgkin's lymphoma, and diffuse large B cell lymphoma.

Exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stein Glioma, Childhood; Brain Tumor, Adult; Brain Tumor, Brain Stern Glioma, Childhood; Brain Tumor, Cerebellar Astrocytoma, Childhood; Brain Tumor, Cerebra Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primaiy; Central Nervous System Lymphoma, Primary; Cerebellar Astrocytoma, Childhood; Cerebra Astrocytoma/ Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Recta Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated and/or prevented in accordance with the methods described herein.

In some embodiments, the tumor is a solid tumor. In some embodiments, the solid tumor is locally advanced or metastatic. In some embodiments, the solid tumor is refractory (e.g., resistant) after standard therapy.

Methods described herein can reduce, ameliorate or altogether eliminate the disorder, and/or its associated symptoms, to keep it from becoming worse, to slow the rate of progression, or to minimize the rate of recurrence of the disorder once it has been initially eliminated (i.e., to avoid a relapse). A suitable dose and therapeutic regimen may vary depending upon the specific compounds, combinations, and/or pharmaceutical compositions used and the mode of delivery of the compounds, combinations, and/or pharmaceutical compositions. In some embodiments, the method increases the average length of survival, increases the average length of progression-free survival, and/or reduces the rate of recurrence, of subjects treated with the combinations described herein in a statistically significant manner.

In some embodiments, the cancer is lung cancer (e.g., non-small cell lung cancer (NSCLC), RAS mutant NSCLC; metastatic cancer), bone cancer, pancreatic cancer, skin cancer, cancer of the head or neck, cutaneous or intraocular melanoma, uterine cancer, ovarian cancer (e.g., unresectable low-grade ovarian, advanced or metastatic ovarian cancer), rectal cancer, cancer of the anal region, stomach cancer, colon cancer, breast cancer (e.g., triple-negative breast cancer (e.g., breast cancer which does not express the genes for the estrogen receptor, progesterone receiptor, and Her2/neu)), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, mesothelioma (e.g., malignant pleural mesothelioma, surgical resectable malignant pleural mesothelioma) or a combination of one or more of the foregoing cancers. In some embodiments, the cancer is metastatic. In some embodiments, the abnormal cell growth is locally recurring (e.g., the subject has a locally recurrent disease, e.g., cancer).

Inventive methods of the present invention contemplate single as well as multiple administrations of a therapeutically effective amount of a combination as described herein, e.g., a FAK inhibitor in combination with a MEK inhibitor. Combinations, e.g., a combination as described herein, e.g., a FAK inhibitor in combination with a MEK inhibitor, can be administered at regular intervals, depending on the nature, severity and extent of the subject's condition. In some embodiments, a combination as described herein, e.g., a FAK inhibitor in combination with a MEK inhibitor, is administered in a single dose. In some embodiments, a combination as described herein, e.g., a FAK inhibitor in combination with a MEK inhibitor, is administered in multiple doses. In some embodiments, a therapeutically effective amount of a combination as described herein, e.g., a FAK inhibitor in combination with a MEK inhibitor, may be administered orally and periodically at regular intervals (e.g., 1, 2, 3, 4, 5, 6, 7, 8, 9, 10 or more times every 1, 2, 3, 4, 5, or 6 days, or every 1, 2, 3, 4, 5, 6, 7, 8, or 9 weeks, or every 1, 2, 3, 4, 5, 6, 7, 8, 9 months or longer).

In some embodiments, a combination as described herein, e.g., a FAK inhibitor in combination with a MEK inhibitor, is administered at. a predetermined interval (e.g., 1, 2, 3, 4, 5, 6, 7, 8, 9, 10 or more times every 1. 2, 3, 4, 5, or 6 days, or every 1, 2, 3, 4, 5, 6, 7, 8, or 9 weeks, or every 1, 2, 3, 4. 5, 6, 7, 8, 9 months or longer).

Cancer Combination Therapies

In some embodiments, the methods and compositions described herein (e.g., a FAK inhibitor in combination with a MEK inhibitor) is administered together with an additional therapy (e.g., cancer treatment). In one embodiment, a mixture of one or more compounds or pharmaceutical compositions may be administered with the combination described herein, e.g., a FAK inhibitor in combination with a MEK inhibitor, to a subject in need thereof. In yet another embodiment, one or more compounds or compositions (e.g., pharmaceutical compositions) may be administered with the combination described herein, e.g., a FAK inhibitor in combination with a MEK inhibitor, for the treatment or avoidance of various diseases, including, for example, cancer, diabetes, neurodegenerative diseases, cardiovascular disease, blood clotting, inflammation, flushing, obesity, aging, stress, etc. In various embodiments, combination therapies comprising a compound or pharmaceutical composition described herein may refer to (1) pharmaceutical compositions that comprise one or more compounds in combination with the combination described herein, e.g., a FAK inhibitor in combination with a MEK inhibitor; and (2) co-administration of one or more compounds or pharmaceutical compositions described herein with the combination described herein, e.g., a FAK inhibitor in combination with a MEK inhibitor, wherein the compound or pharmaceutical composition described herein have not been formulated in the same compositions. In some embodiments, the combinations described herein (e.g., a FAK inhibitor in combination with a MEK inhibitor) is administered with an additional treatment (e.g., an additional cancer treatment). In some embodiments, the additional treatment (e.g., an additional cancer treatment) can be administered simultaneously (e.g., at the same time), in the same or in separate compositions, or sequentially. Sequential administration refers to administration of one treatment before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional, e.g., secondary, treatment (e.g., a compound or therapy). The order of administration of the first and secondary compound or therapy can also be reversed.

Exemplary cancer treatments include, for example: chemotherapy, targeted therapies such as antibody therapies, immunotherapy, and hormonal therapy. Examples of each of these treatments are provided below.

Chemotherapy

In some embodiments, a combination described herein (e.g., a FAK inhibitor in combination with a MEK inhibitor) is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target. all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclornol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, idarubiein, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time or sequentially. Often, two or more chemotherapy agents are used as combination chemotherapy. In some embodiments, the chemotherapy agents (including combination chemotherapy) can be used in combination with a combination described herein (e.g., a FAK inhibitor in combination with a MEK inhibitor).

Targeted Therapy

In some embodiments, a combination described herein (e.g., a FAK inhibitor in combination with a MEK inhibitor) is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-depdendent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary anbitodies include Ctuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a combination described herein (e.g., a FAK inhibitor in combination with a MEK inhibitor).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a combination described herein (e.g., a FAK inhibitor in combination with a MEK inhibitor) is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in subjects with renal cell carcinoma and melanoma.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a combination as described herein, e.g., a FAK inhibitor in combination with a MEK inhibitor.

Hormonal Therapy

In some embodiments, a combination described herein (e.g., a FAK inhibitor in combination with a MEK inhibitor) is administered with a hormonal therapy. The growth of sonic cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a combination described herein (e.g., a FAK inhibitor in combination with a MEK inhibitor).

Radiation Therapy

The combinations described herein (e.g., a FAK inhibitor in combination with a MEK inhibitor) can be used in combination with directed energy or particle, or radioisotope treatments, e.g., radiation therapies, e.g., radiation oncology, for the treatment of proliferative disease, e.g., cancer, e.g., cancer associated with cancer stem cells. The combinations described herein (e.g., a FAK inhibitor in combination with a MEK inhibitor) may be administered to a subject simultaneously or sequentially along with the directed energy or particle, or radioisotope treatments. For example, the combinations described herein (e.g., a FAK inhibitor in combination with a MEK inhibitor) may be administered before, during, or after the directed energy or particle, or radioisotope treatment, or a combination thereof. The directed energy or particle therapy may comprise total body irradiation, local body irradiation, or point irradiation. The directed energy or particle may originate from an accelerator, synchrotron, nuclear reaction, vacuum tube, laser, or from a radioisotope. The therapy may comprise external beam radiation therapy, teletherapy, brachytherapy, sealed source radiation therapy, systemic radioisotope therapy, or unsealed source radiotherapy. The therapy may comprise ingestion of, or placement in proximity to, a radioisotope, e.g., radioactive iodine, cobalt, cesium, potassium, bromine, fluorine, carbon. Externa beam radiation may comprise exposure to directed alpha particles, electrons (e.g., beta particles), protons, neutrons, positrons, or photons (e.g., radiowave, millimeter wave, microwave, infrared, visible, ultraviolet, X-ray, or gamma-ray photons). The radiation may be directed at any portion of the subject in need of treatment.

Surgery

The combinations described herein (e.g., a FAK inhibitor in combination with a MEK inhibitor) can be used in combination with surgery, e.g., surgical exploration, intervention, biopsy, for the treatment of proliferative disease, e.g., cancer, e.g., cancer associated with cancer stem cells. The combinations described herein (e.g., a FAK inhibitor in combination with a MEK inhibitor) may be administered to a subject simultaneously or sequentially along with the surgery. For example, the combinations described herein (e.g., a FAK inhibitor in combination with a MEK inhibitor) may be administered before (pre-operative), during, or after (post-operative) the surgery, or a combination thereof. The surgery may be a biopsy during which one or more cells are collected for further analysis. The biopsy may be accomplished, for example, with a scalpel, a needle, a catheter, an endoscope, a spatula, or scissors. The biopsy may be an excisional biopsy, an incisional biopsy, a core biopsy, or a needle biopsy, e.g., a needle aspiration biopsy. The surgery may involve the removal of localized tissues suspected to be or identified as being cancerous. For example, the procedure may involve the removal of a cancerous lesion, lump, polyp, or mole. The procedure may involve the removal of larger amounts of tissue, such as breast, bone, skin, fat, or muscle. The procedure may involve removal of part of, or the entirety of, an organ or node, for example, lung, throat, tongue, bladder, cervix, ovary, testicle, lymph node, liver, pancreas, brain, eye, kidney, gallbladder, stomach, colon, rectum, or intestine. In one embodiment, the cancer is breast cancer, e.g., triple negative breast cancer, and the surgery is a mastectomy or lumpectomy.

Anti-Inflammatory Agents

A combination described herein (e.g., a FAK inhibitor in combination with a MEK inhibitor), can be administered with an anti-inflammatory agent. Anti-inflammatory agents can include, but are not limited to, non-steroidal anti-inflammatory agents (e.g., Salicylates (Aspirin (acetylsalicylic acid), Diflunisal, Salsalate), Propionic acid derivatives (Ibuprofen, Naproxen, Fenoprofen, Ketoprofen, Flurbiprofen, Oxaprozin, Loxoprofen), Acetic acid derivatives (Indomethacin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives (Fenamates)(Mefenamic acid, Meciofenamic acid, Flufenamic acid, Tolfenamic acid), Selective COX-2 inhibitors (Coxibs) (Celecoxib), Sulphonanilides (Nimesulide). Steriods (e.g. Hydrocortisone (Cortisol), Cortisone acetate, Prednisone, Prednisolone, Methylprednisolone, Dexamethasone, Betamethasone, Triamcinolone, Beclometasone, Fludrocortisone acetate, Deoxycorticosterone acetate, Aldosterone).

Analgesic Agents

Analgesics can include but are not limited to, opiates (e.g. morphine, codeine, oxycodone, hydrocodone, dihydromorphine, pethidine, buprenorphine, tramadol, venlafaxine), paracetomal and Non-steroidal anti-inflammatory agents (e.g., Salicylates (Aspirin (acetylsalicylic acid), Diflunisal, Salsalate), Propionic acid derivatives (Ibuprofen, Naproxen, Fenoprofen, Ketoprofen, Flurbiprofen, Oxaprozin, Loxoprofen), Acetic acid derivatives (Indomethacin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives (Fenamates)(Mefenamic acid, Meclofenamic acid, Flufenamic acid, Tolfenamic acid), Selective COX-2 inhibitors (Coxibs) (Celecoxib), Sulphonanilides (Nimesulide).

Antiemetic Agents

A combination described herein (e.g., a FAK inhibitor in combination with a MEK inhibitor), can be administered with an antiemetic agent. Antiemetic agents can include, but are not limited to, 5-HT3 receptor antagonists (Dolasetron (Anzemet), Granisetron (Kytril, Sancuso), Ondansetron (Zofran), Tropisetron (Navoban), Palonosetron (Aloxi), Mirtazapine (Remeron)), Dopamine antagonists (Domperidone, Olanzapine, Droperidol, Haloperidol, Chlorpromazine, Promethazine, Prochlorperazine, Metoclopramide (Reglan), Alizapride, Prochlorperazine (Compazine, Stemzine, Buccastem, Stemetil, Phenotil), NK1 receptor antagonist (Aprepitant (Emend), Antihistamines (Cyclizine, Diphenhydramine (Benadryl), Dimenhydrinate (Gravol, Dramamine), Meclozine (Bonine, Antivert), Promethazine (Pentazine, Phenergan, Promacot), Hydroxyzine), benzodiazapines (Lorazepam, Midazolam), Anticholinergics (hyoscine), steroids (Dexamethasone).

Administration and Dosage

The combinations of this invention may be administered orally, parenterally, topically, rectally, or via an implanted reservoir, preferably by oral administration or administration by injection. In some cases, the pH of the composition (e.g., pharmaceutical composition) may be adjusted with pharmaceutically acceptable acids, bases or buffers to enhance the stability or efficacy of the composition.

In some embodiments, the subject is administered the composition (e.g., pharmaceutical composition) orally. In some embodiments the composition (e.g., pharmaceutical composition) is be orally administered in any orally acceptable dosage form including, but not limited to, liqui-gel tablets or capsules, syrups, emulsions and aqueous suspensions. Liqui-gels may include gelatins, plasticisers, and/or opacifiers, as needed to achieve a suitable consistency and may he coated with enteric coatings that are approved for use, e.g., shellacs. Additional thickening agents, for example gums, e.g., xanthum gum, starches, e.g., corn starch, or glutens may be added to achieve a desired consistency of the composition (e.g., pharmaceutical composition) when used as an oral dosage. If desired, certain sweetening and/or flavoring and/or coloring agents may be added.

In some embodiments, the subject is administered the composition (e.g., pharmaceutical composition) in a form suitable for oral administration such as a tablet, capsule, pill, powder, sustained release formulations, solution, and suspension. The composition (e.g., pharmaceutical composition) may be in unit dosage forms suitable for single administration of precise dosages. Pharmaceutical compositions may comprise, in addition to a compound as described herein (e.g., a FAK inhibitor (e.g., VS-6063 or a pharmaceutically acceptable salt. thereof); a MEK inhibitor (e.g., pimasertib or a pharmaceutically acceptable salt thereof)), a pharmaceutically acceptable carrier, and may optionally further comprise one or more pharmaceutically acceptable excipients, such as, for example, stabilizers, diluents, binders, and lubricants. In addition, the tablet may include other medicinal or pharmaceutical agents, carriers, and or adjuvants. Exemplary pharmaceutical compositions include compressed tablets (e.g., directly compressed tablets), e.g., comprising a FAK inhibitor (e.g., VS-6063 or a pharmaceutically acceptable salt thereof); or a MEK inhibitor (e.g., pimasertib or a pharmaceutically acceptable salt thereof), Tablets are also provided comprising the active or therapeutic ingredient (e.g., compound as described herein (e.g., a FAK inhibitor (e.g., VS-6063 or a pharmaceutically acceptable salt thereof); a MEK inhibitor (e.g., pimasertib or a pharmaceutically acceptable salt thereof))). In addition to the active or therapeutic ingredients, tablets may contain a number of inert materials such as carriers. Pharmaceutically acceptable carriers can be sterile liquids, such as water and oils, including those of petroleum, animal, vegetable or synthetic origin, such as peanut oil, sesame oil and the like. Saline solutions and aqueous dextrose can also be employed as liquid carriers. Oral dosage forms for use in accordance with the present invention thus may be formulated in conventional manner using one or more pharmaceutically acceptable carriers comprising excipients and auxiliaries, which facilitate processing of the active ingredients into preparations which, can be used pharmaceutically.

Excipients can impart good powder flow and compression characteristics to the material being compressed. Examples of excipients are described, for example, in the Handbook of Pharmaceutical Excipients ($5^{th}$ edition), Edited by Raymond C Rowe, Paul J. Sheskey, and Sian C. Owen; Publisher: Pharmaceutical Press.

For oral administration, the active ingredients, e.g., the compound as described herein (e.g., a FAK inhibitor (e.g., VS-6063 or a pharmaceutically acceptable salt thereof); a MEK inhibitor (e.g., pimasertib or a pharmaceutically acceptable salt. thereof)), can be formulated readily by combining the active ingredients with pharmaceutically acceptable carriers well known in the art. Such carriers enable the active ingredients of the invention to be formulated as tablets, pills, capsules, liquids, gels, syrups, slurries, powders or granules, suspensions or solutions in water or non-aqueous media, and the like, for oral ingestion by a subject. Pharmacological preparations for oral use can be made using a solid excipient, optionally grinding the resulting mixture, and processing the mixture of granules, after adding suitable auxiliaries if desired, to obtain, for example, tablets. Suitable excipients such as diluents, binders or disintegrants may be desirable.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics"). Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician. A course of therapy can comprise one or more separate administrations of a compound as described herein (e.g., a FAK inhibitor, a MEK inhibitor). A course of therapy can comprise one or more cycles of a compound as described herein (e.g., a FAK inhibitor, a MEK inhibitor).

In some embodiments, a cycle, as used herein in the context of a cycle of administration of a drug, refers to a period of time for which a drug is administered to a patient. For example, if a drug is administered for a cycle of 21 days, the periodic administration, e.g., daily or twice daily, is given for 21 days. A drug can be administered for more than one cycle. Rest periods may be interposed between cycles. A rest cycle may be 1, 2, 4, 6, 8, 10, 12, 16, 20, 24 hours, 1, 2, 3, 4, 5, 6, 7 days, or 1, 2, 3, 4 or more weeks in length.

Oral dosage forms may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

EXAMPLES

The disclosure is further described in the following examples, which do not limit the scope of the claims.

Materials and Methods

Cell Lines: Cancer cell lines were purchased from American Type Culture Collection (Manassas, VA) and cultured under ATCC recommended standard culture conditions. Mero-41 (mesothelioma cell line) were purchased from Sigma-Aldrich (St. Louis, MO) and cultured under ECACC recommended standard culture conditions. MDA-MB-231 (triple negative breast cancer cell line) were cultured under ECACC recommended standard culture conditions. TOV-21G (ovarian clear cell carcinoma cell line) were cultured under ECACC recommended standard culture conditions. Growth media for all cell lines were supplemented with penicillin (100 units/ml)/streptomycin (100 µg/ml). Medium included a 1:1 mixture of MCDB 105 medium ((+1.5 g/L sodium bicarbonate): Medium 199 (+2.2 g/L sodium bicarbonate); 15% FBS.

A. Combination Screen Format:

A full 9×9 matrix format was used to evaluate the combination effect between VS-6063 and MEK inhibitors across a wide concentration range and dose ratios. Compound were used at the top concentration 10 uM in a 2-fold dilution. Paclitaxel was dosed at the top concentration 1 uM in a 3-fold dilution.

B. Assays

A 'Matrigel on-top' (MoT) assay where cells were propagated in a 3-dimentional culture was used. Cells were plated above a dense base layer of Matrigel (BD Biosciences, Franklin Lakes, N.J.), diluted 1:1 with culture medium. Single cell preparations were resuspended in dilute Matrigel (1:50 in culture medium) and seeded to cover the Matrigel base layer. This ensured that ovarian cancer cells were surrounded with extracellular matrix (ECM) components, of which collagen and laminin are the major Matrigel constituents. Cells were seeded in a density of 500 cells per well in 384-well black Ultra-low attachment plates with clear bottom (Corning, Tewksbury MA). Twenty-four hours after incubation, cells were treated with VS-6063 at various concentrations, or a combination of VS-6063 and MEK inhibitor at various concentrations. Cell survival/proliferation was assessed by CellTiter-Glo® Luminescent Cell Viability Assay (Promega, Madison, Wis.). A $T_0$ reading (when compound was added) and a $T_{96}$ reading (96 hours incubation with the compounds) were obtained using Envision 2104 Multilabel Reader (PerkinElmer, Boston, Mass.).

C. Combination Analytical Methods

Combination effects were evaluated by comparing the averaged viability/inhibition to three different null reference models derived from the single agent activities.

Bliss Independence Mode

Bliss independence model predicts interaction effects with the assumption that single agents act in a mutually non-exclusive manner and each agent contributes independently to the resulting effect (Bliss et al, 1939). The expected additivity effect is the statistical expectation for the combined effect from independent inhibitors: Mathematically, Bliss $(F_U) = F_{UA1} \times F_{UA2}$, where $F_{UA1}$ and $F_{UA2}$ are the unaffected fraction when treated with compounds A1 and A2, respectively.

Highest Single Agent (HSA) Model/Gaddum's Non-Interaction Mode

Gaddum's non-interaction model states that the single agents must necessarily be helping each other if the effect of a combination exceeds either of the single agents (Berenbaum et al, 1989). Mathmatically, HSA $(F_a) = \max(Fa_{A1}, Fa_{A2})$, where $Fa_{A1}$ and $Fa_{A2}$ are the affected fraction when treated with compounds A1 and A2, respectively.

Loewe Additivity Mode

Loewe additivity model assumes that two inhibitors act on a target through a similar mechanism and that the inhibitors differ only in potencies (Fitzgerald et al, 2006). Combination effect over Loewe additivity model can be considered as a decrease in the total effective drug dose in combination compared to that of the single agents required to achieve a given effect level. Synergy can be measured in term of combination index, $CI = D_{A1}/d_{A1} + D_{A2}/d_{A2}$ where $D_{A1}$ and $D_{A2}$ are the combination doses of compounds A1 and A2; $d_{A1}$ and $d_{A2}$ are the single agent doses of compounds A1 and A2 at the same affected fraction achieved by the combination doses, CI<1 for synergistic combinations and CI>1 for antagonistic combinations. Loewe $(F_a)$ is the affected fraction that satisfies $(D_{A1}/d_{A1(Loewe)}) + (D_{A2}/d_{A2(Loewe)}) = 1$ where $d_{A1(Loewe)}$ and $d_{A2(Loewe)}$ are the effective concentration at Loewe $(F_a)$ of the single agent compounds A1 and A2.

Results

Figure 1B:
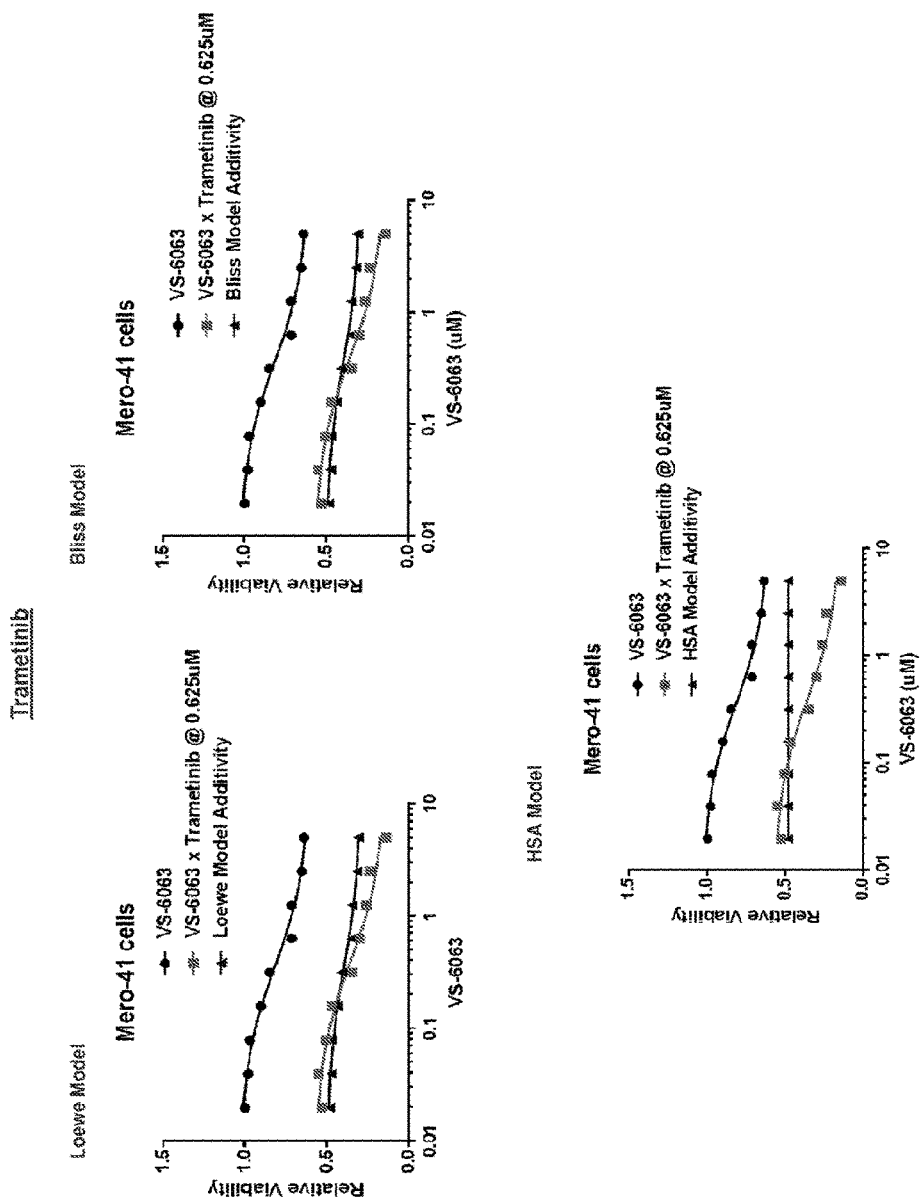
Figure 2:
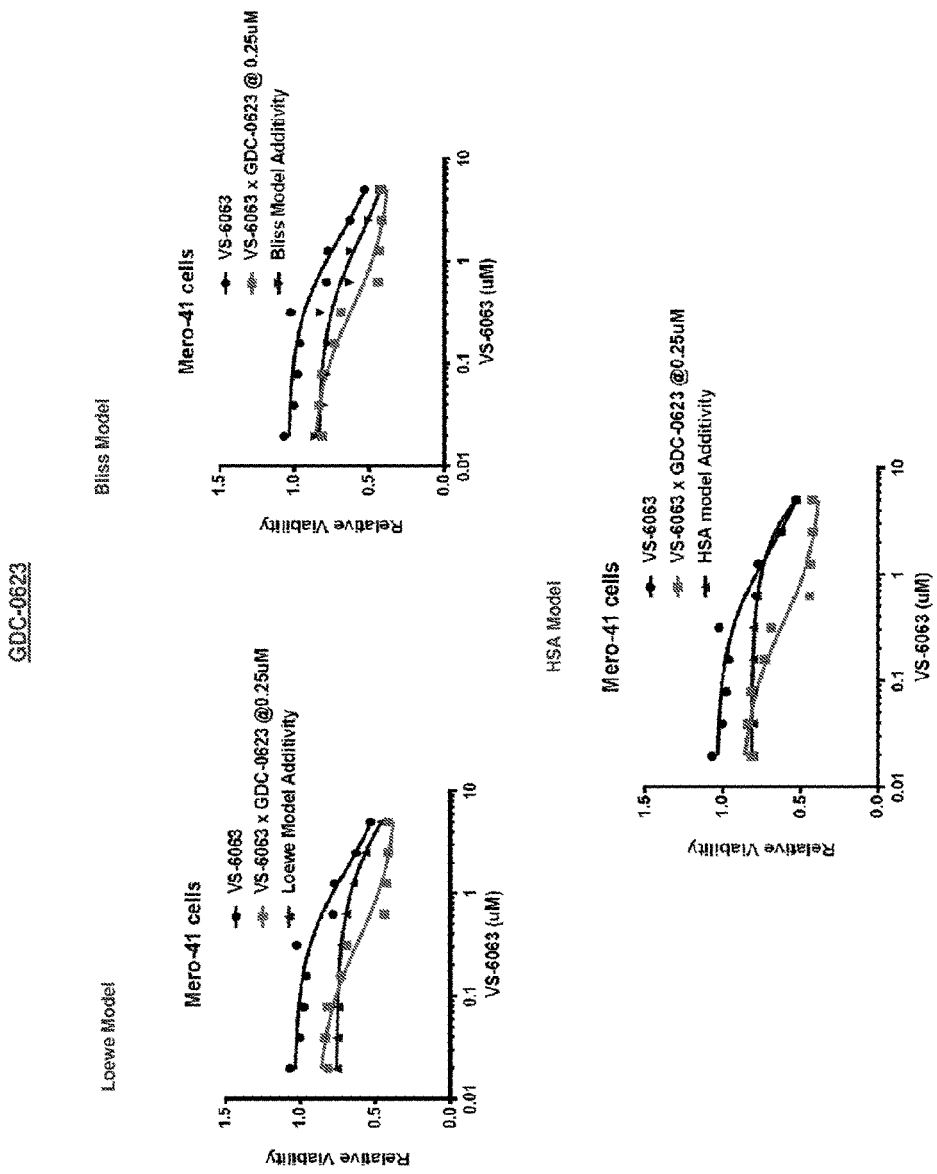
FIG. 2 shows exemplary plots of mesothelioma cell viability with increasing concentrations of VS-6063, an exemplary FAK inhibitor, with and without GDC-6023, an exemplary MEK inhibitor.
Figure 3:
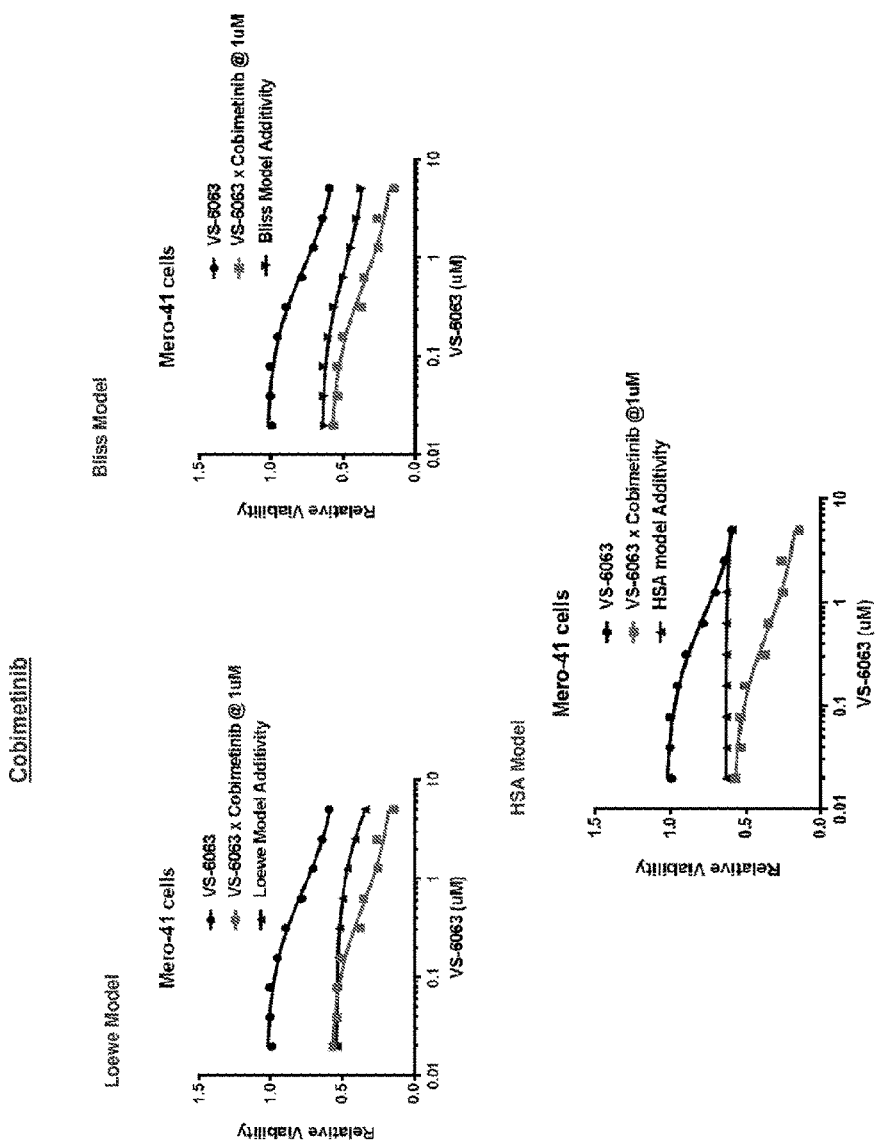
FIG. 3 shows exemplary plots of mesothelioma cell viability with increasing concentrations of VS-6063, an exemplary FAK inhibitor, with and without cobimetinib, an exemplary MEK inhibitor.
Figure 4:
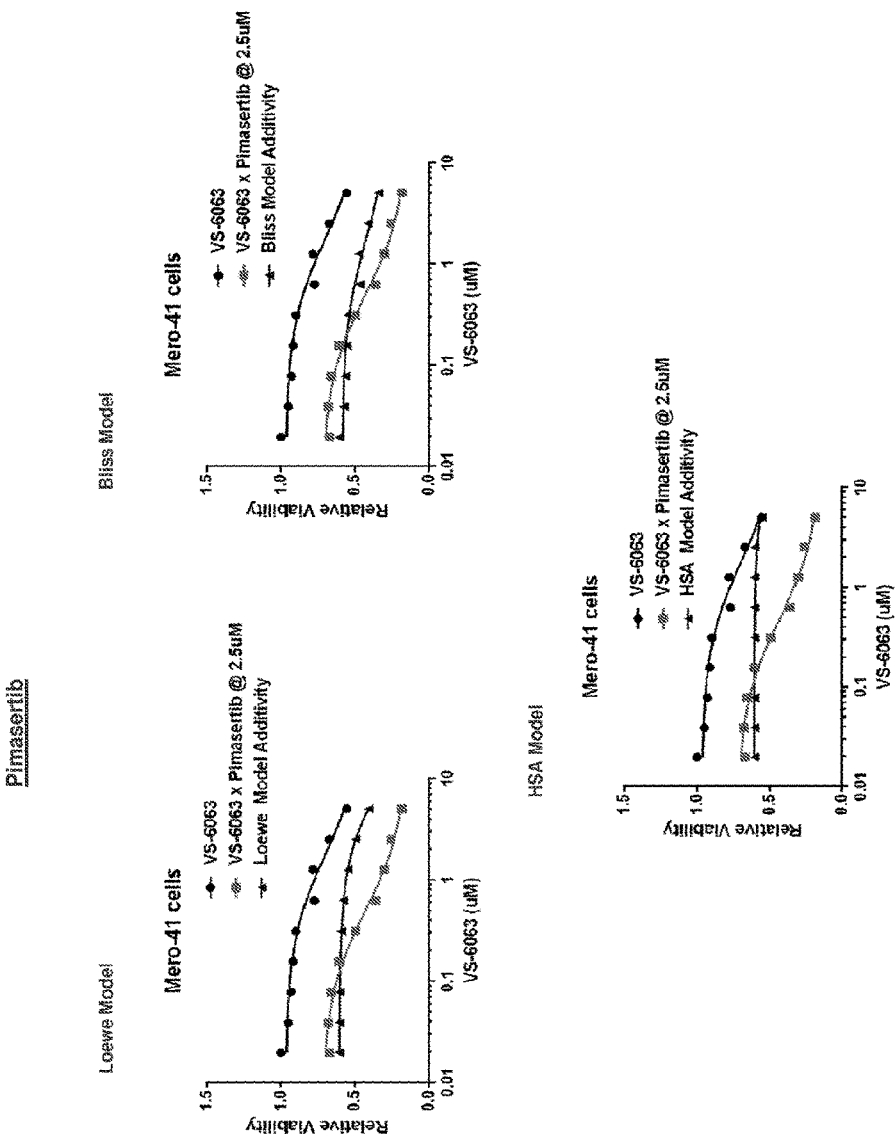
FIG. 4 shows exemplary plots of mesothelioma cell viability with increasing concentrations of VS-6063, an exemplary FAK inhibitor, with and without pimasertib, an exemplary MEK inhibitor.
Figure 5:
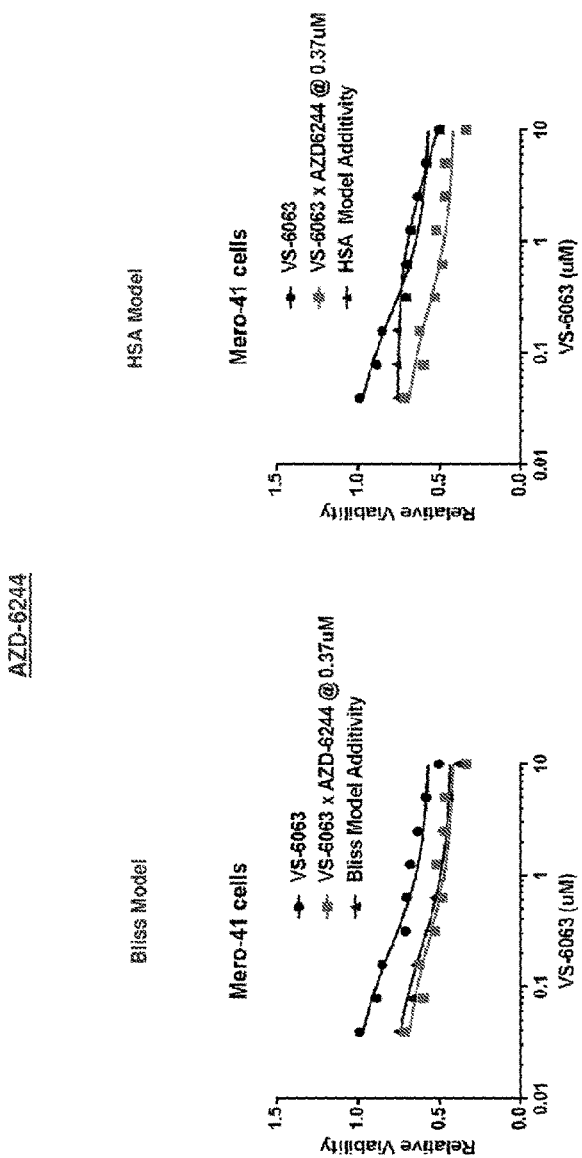
FIG. 5 shows exemplary plots of mesothelioma cell viability with increasing concentrations of VS-6063, an exemplary FAK inhibitor, with and without AZD6244, an exemplary MEK inhibitor.
Figure 6:
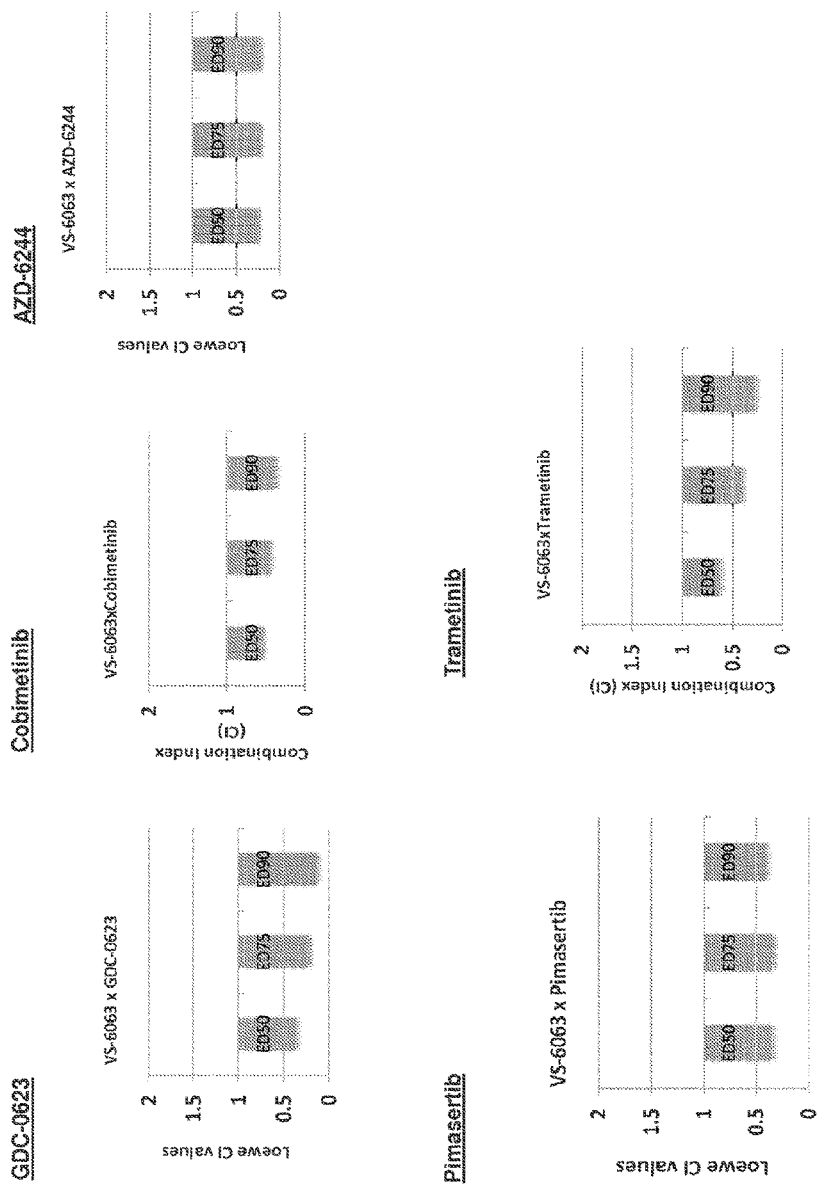
FIG. 6 shows exemplary combination index analyses for VS-6063, an exemplary FAK inhibitor, with GDC-0623. cobimetinib, AZD-6244, pimasertib, and trametinib in mesothelioma cells.
Figure 7:
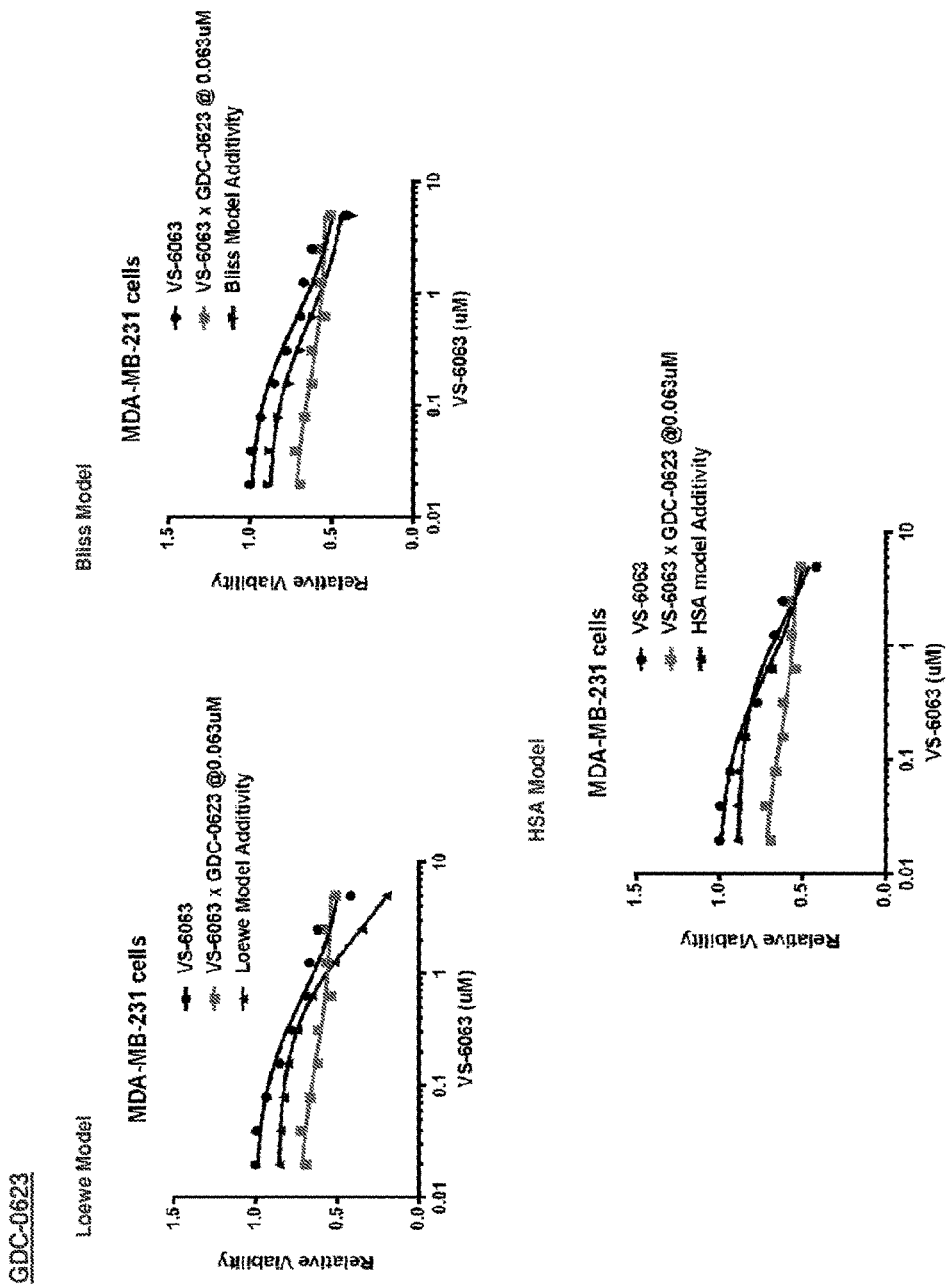
FIG. 7 shows exemplary plots of breast cancer cell viability with increasing concentrations of VS-6063, an exemplary FAK inhibitor, with and without GDC-6023, an exemplary MEK inhibitor.
Figure 8:
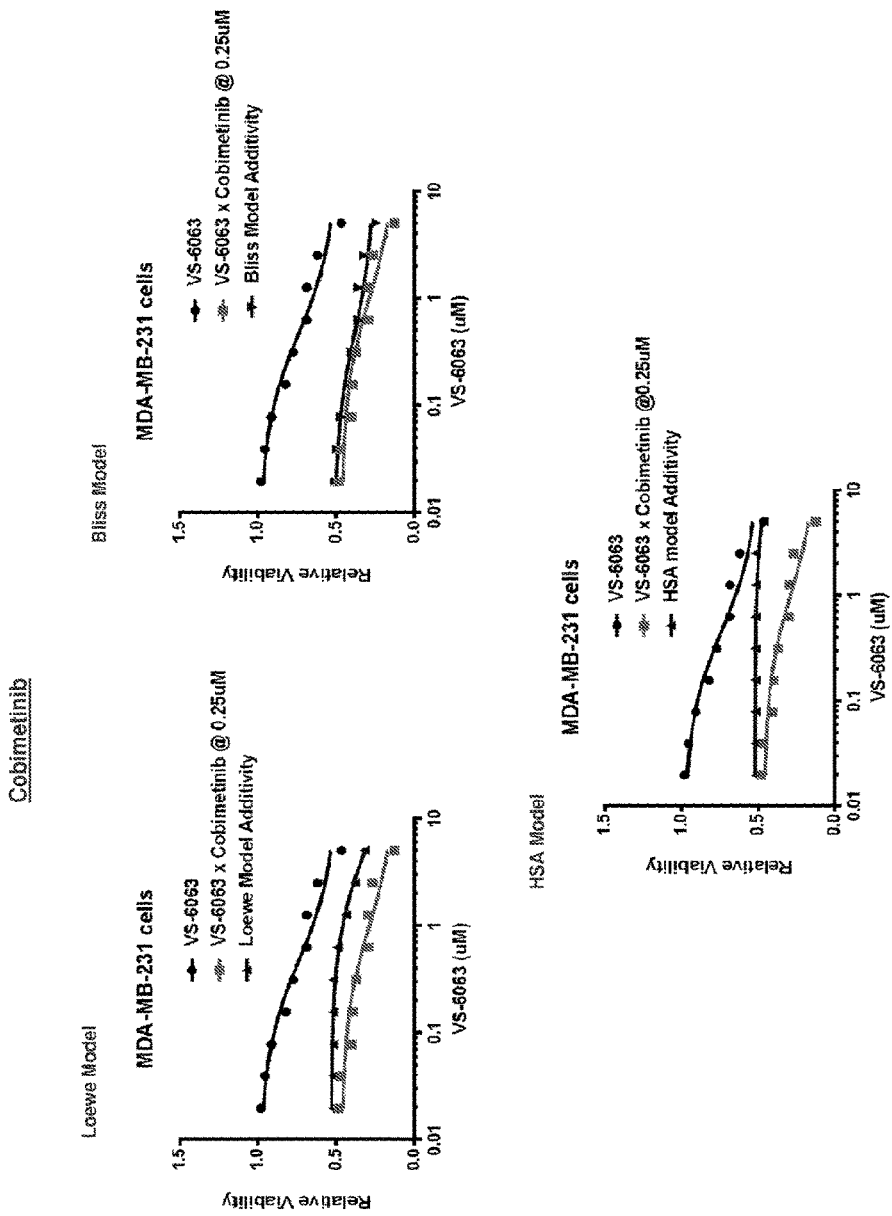
FIG. 8 shows exemplary plots of breast cancer cell viability with increasing concentrations of VS-6063, an exemplary FAK inhibitor, with and without cobimetinib, an exemplary MEK inhibitor.
Figure 9:
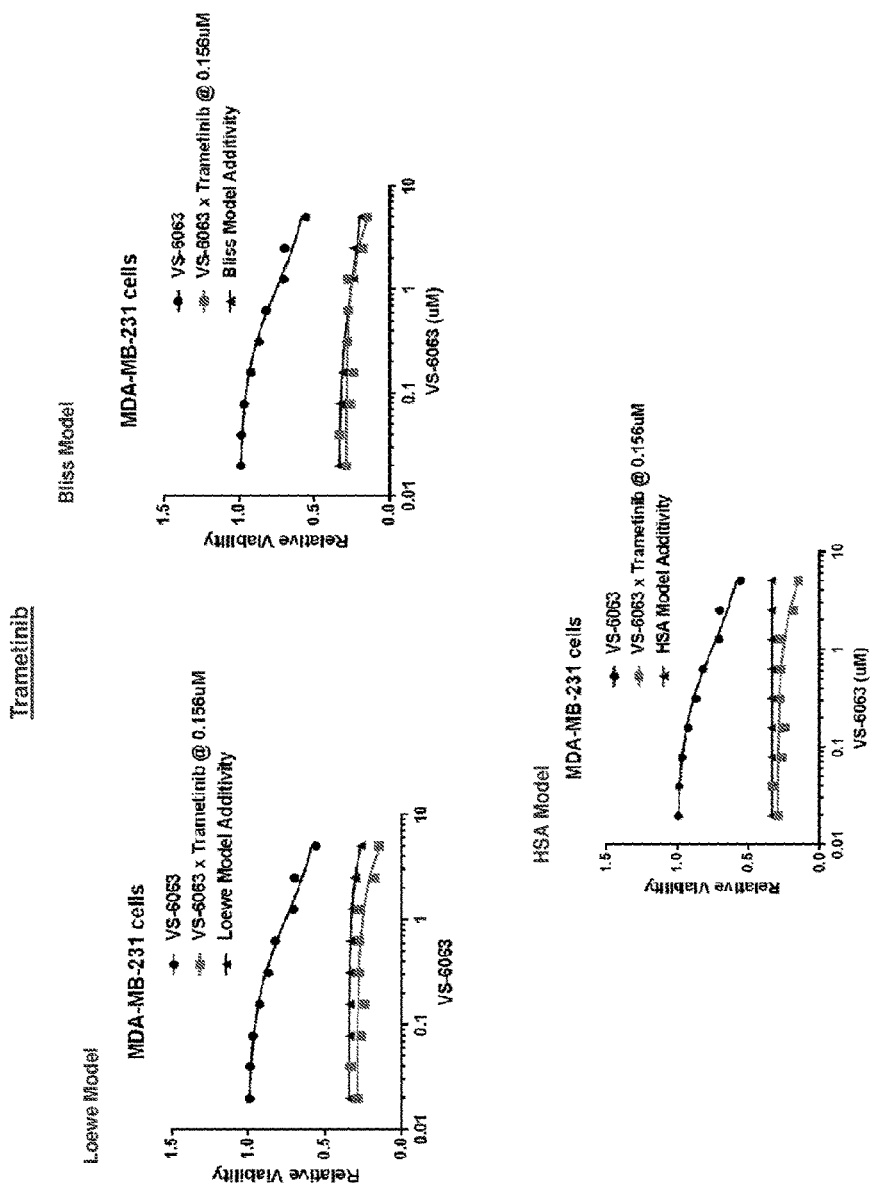
FIG. 9 shows exemplary plots of breast cancer cell viability with increasing concentrations of VS-6063, an exemplary FAK inhibitor, with and without tramatinib, an exemplary MEK inhibitor.
Figure 10:
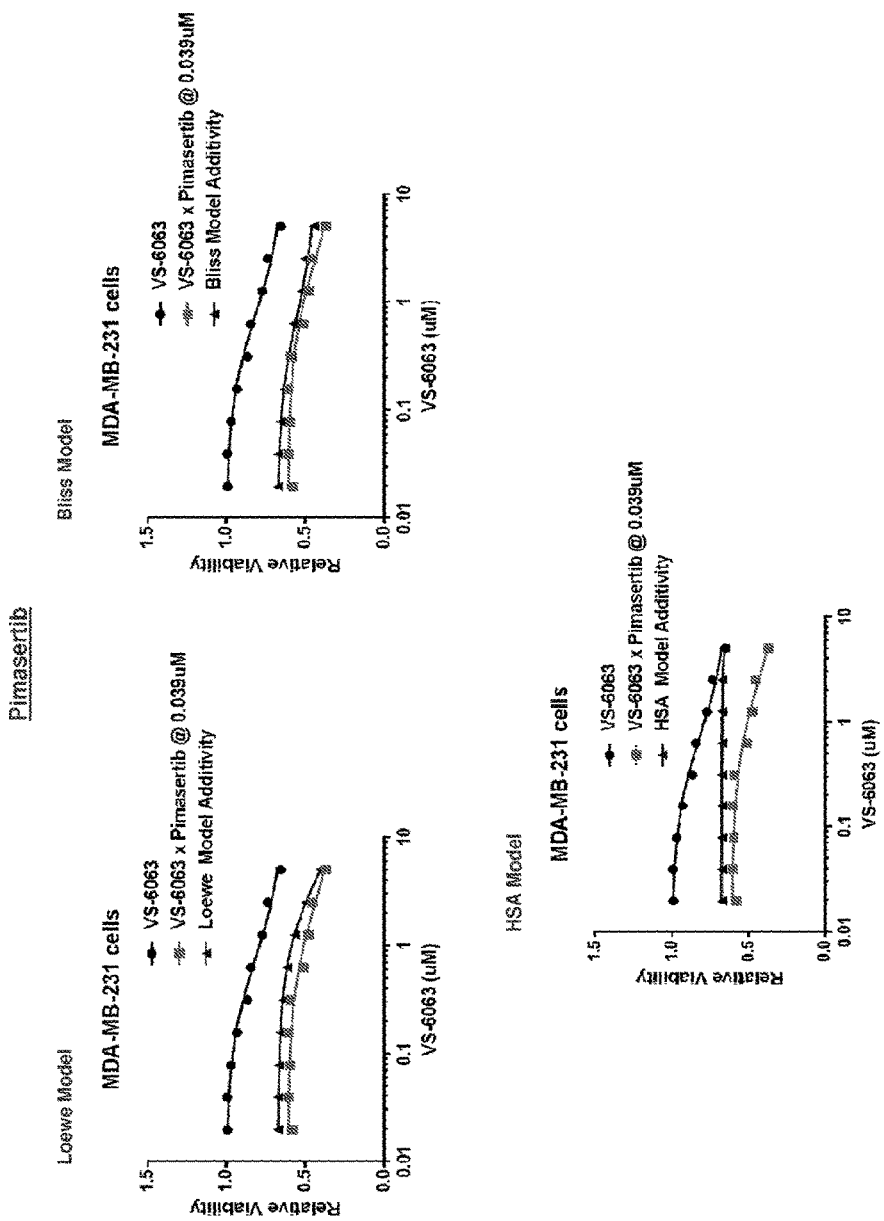
FIG. 10 shows exemplary plots of breast cancer cell viability with increasing concentrations of VS-6063, an exemplary FAK inhibitor, with and without pimasertib, an exemplary MEK inhibitor.
Figure 11:
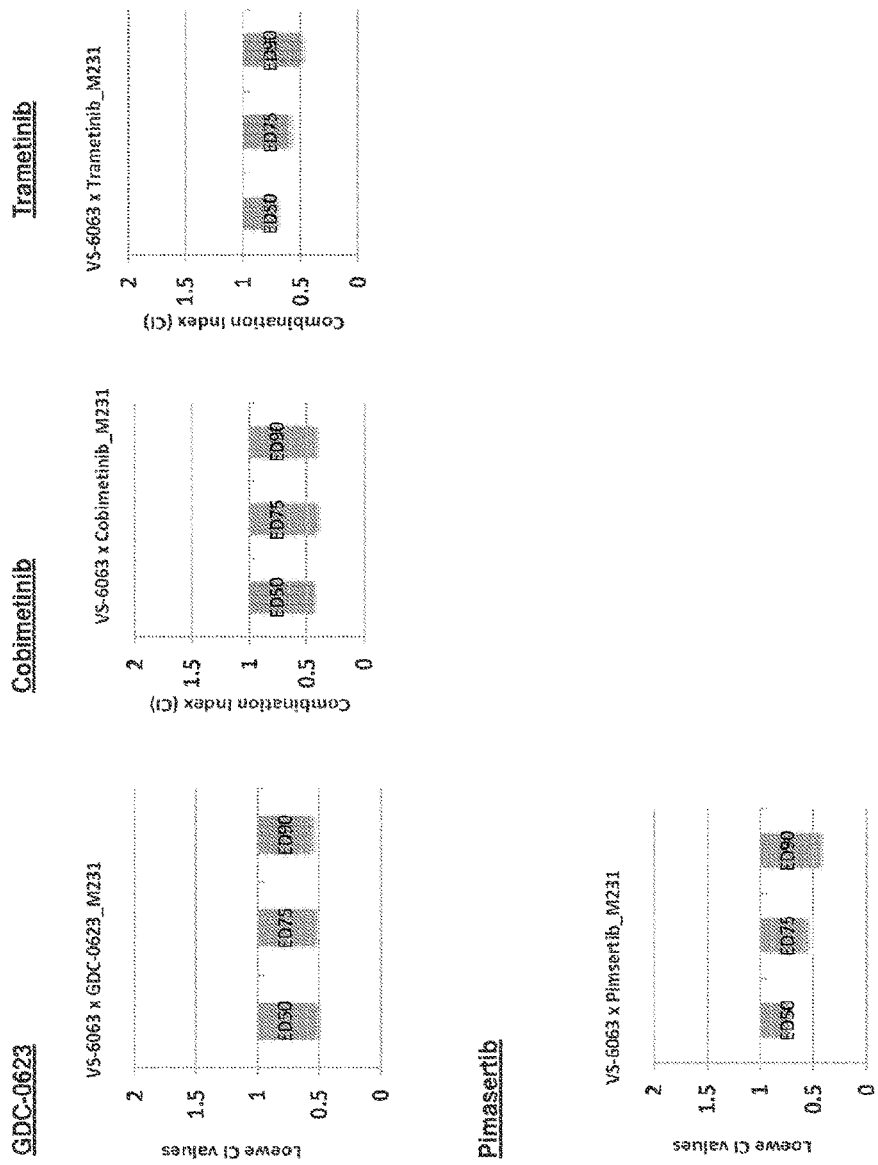
FIG. 11 shows exemplary combination index analyses for VS-6063, an exemplary FAK inhibitor, with GDC-0623, cobimetinib, trametinib, and pimasertib in breast cancer cells.
Figure 12:
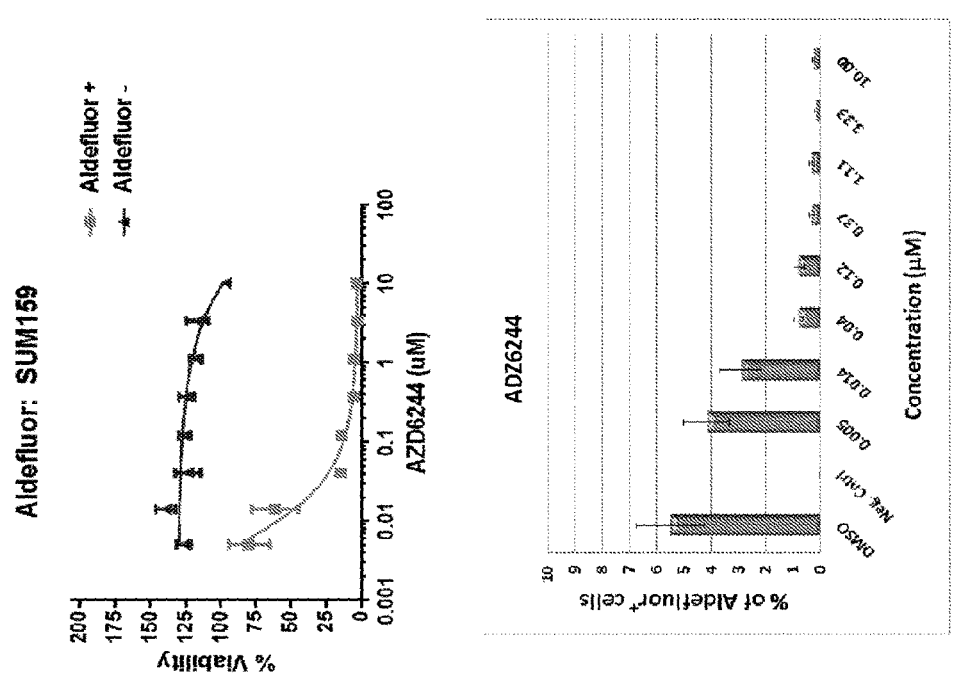
FIG. 12 shows exemplary plots of cancer stern cell viability with increasing concentrations of AZD6244, an exemplary MEK inhibitor.
Figure 13:
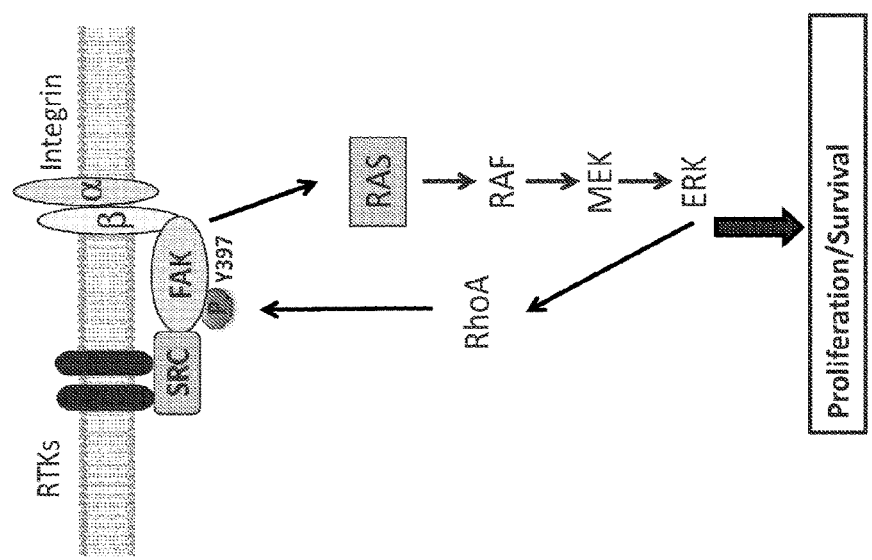
FIG. 13 shows potential pathways that FAK and MEK inhibitors may interact.

FIGS. 1 to 12 show exemplary plots and analyses of cell viability of mesothelioma and breast cancer cells in the presence of exemplary FAK inhibitor VS-6063 with and without exemplary MEK inhibitors GDC-0623, cobimetinib, AZD-6244, pimasertib, and trametinib. Comparative plots of viability in the presence and absence of MEK inhibitors suggest a more than additive effect (e.g., a synergistic effect) of the combination of a FAK inhibitor, e.g., VS-6063, and a MEK inhibitor (e.g., GDC-0623, cobimetinib, AZD-6244, pimasertib, and trametinib). Plots modeling the combination effects (e.g., Bliss Independence Model, Highest Single Agent (HSA) Model, and Loewe Additivity Model) are included which show how the activity (e.g., effect on cell viability) of the given combination of FAK and MEK inhibitors would appear on the plot. based on an additive effect of inhibition of the two inhibitors.

REFERENCES

1. Bliss, C. (1939). The toxicity of poisons applied jointly. Annals of Applied Biology, 26:585-615
2. Berenbaum, M. C. (1989). What is synergy? Pharmacology Review, 41:93-141

3. Fitzgerald, J. B. et. al. (2006). System biology and combination therapy in the quest for clinical efficacy. Nature Chemical Biology, 2:458-466

What is claimed is:

1. A method of treating a subject having cancer, the method comprising administering to the subject a therapeutically effective amount of VS-6063, or a pharmaceutically acceptable salt thereof, administered at between 1 to 500 mg, in combination with a MEK inhibitor selected from GDC 0623, cobimetinib, trametinib, pimasertib, AZD6244, or a pharmaceutically acceptable salt thereof, thereby treating the subject, wherein the cancer is selected from mesothelioma and breast cancer.

2. The method of claim 1, wherein VS-6063 or the MEK inhibitor is administered orally.

3. The method of claim 1, wherein VS-6063, or a pharmaceutically acceptable salt thereof is present in the composition comprising 5 to 30% weight of VS-6063, or a pharmaceutically acceptable salt thereof, per weight of the composition.

4. The method of claim 1, wherein the MEK inhibitor is trametinib, or a pharmaceutically acceptable salt thereof.

5. The method of claim 1, wherein the MEK inhibitor is GDC-0623, or a pharmaceutically acceptable salt thereof.

6. The method of claim 1, wherein the MEK inhibitor is cobimetinib, or a pharmaceutically acceptable salt thereof.

7. The method of claim 1, wherein the MEK inhibitor is AZD6244, or a pharmaceutically acceptable salt thereof.

8. The method of claim 1, wherein the MEK inhibitor is pimasertib, or a pharmaceutically acceptable salt thereof.

9. The method of claim 1, wherein the administration is performed in combination with administration of an additional cancer therapy agent.

10. The method of claim 9, wherein the cancer therapy is chemotherapy, targeted therapies, immunotherapy, or hormonal therapy.

11. The method of claim 9, wherein the cancer therapy comprises administration of an anti-inflammatory agent, analgesic agent, or antiemetic agent.

* * * * *